US012558509B2

(12) United States Patent
  Chuah et al.

(10) Patent No.:  US 12,558,509 B2
(45) Date of Patent:  Feb. 24, 2026

(54) HEADGEAR WITH TENSION LIMIT DETECTION FEATURE

(71) Applicant: ResMed Asia Pte. Ltd., Singapore (SG)

(72) Inventors: Teong Hong Chuah, Singapore (SG); Ramyabai Gunalan, Singapore (SG); Han Seong Chew, Singapore (SG); Jing Wen Tam, Singapore (SG)

(73) Assignee: ResMed Asia Pte. Ltd., Singapore (SG)

( * ) Notice: Subject to any disclaimer, the term of this patent is extended or adjusted under 35 U.S.C. 154(b) by 756 days.

(21) Appl. No.: 17/945,251

(22) Filed: Sep. 15, 2022

(65) Prior Publication Data
  US 2023/0087696 A1    Mar. 23, 2023

(30) Foreign Application Priority Data
  Sep. 17, 2021    (SG) ............................ 10202110289T

(51) Int. Cl.
  *A61M 16/06*        (2006.01)
  *A61M 16/08*        (2006.01)
(52) U.S. Cl.
  CPC .... *A61M 16/0694* (2014.02); *A61M 16/0816* (2013.01); *A61M 16/0616* (2014.02)
(58) Field of Classification Search
  CPC .... A61M 16/06–0694; A61M 16/0816; A62B 18/02; A62B 18/025; A62B 23/02; A62B 23/025
  See application file for complete search history.

(56) References Cited

U.S. PATENT DOCUMENTS 4,782,832 A    11/1988  Trimble et al.
4,944,310 A    7/1990  Sullivan
      (Continued)

FOREIGN PATENT DOCUMENTS

WO    WO 98/004310 A1    2/1998
WO    WO 98/034665 A1    8/1998
      (Continued)

OTHER PUBLICATIONS

"*Respiratory Physiology*", by John B. West, Lippincott Williams & Wilkins, 9th edition published 2012 (8 pages).
      (Continued)

*Primary Examiner* — Valerie L Woodward
(74) *Attorney, Agent, or Firm* — Nixon & Vanderhye P.C.

(57) ABSTRACT

Headgear for a patient interface includes one or more straps each having a first end for connecting to a mask. The first end of each strap includes a connection portion which is grippable by a user to pull the strap to increase a tension in the strap, a first rigid member and a second rigid member that extends from a resilient carrier that is connected to the connection portion. The second rigid member is movable relative to the first rigid member when the connection portion is pulled. At least part of the second rigid member is arranged to strike the first rigid member to cause at least an audible alert when the second rigid member travels further than a threshold distance. The resilient carrier is constructed and arranged such that the threshold distance corresponds to a desired tension limit for the strap.

19 Claims, 22 Drawing Sheets

(56)　　　　References Cited

U.S. PATENT DOCUMENTS

| | | | | |
|---|---|---|---|---|
| 5,687,715 | A | 11/1997 | Landis | |
| 6,532,959 | B1 | 3/2003 | Berthon-Jones | |
| 6,581,594 | B1 | 6/2003 | Drew et al. | |
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 10,960,239 | B2 | 3/2021 | Henry et al. | |
| 2007/0028919 | A1* | 2/2007 | Ho | A61M 16/0633 |
| | | | | 128/204.18 |
| 2008/0083412 | A1* | 4/2008 | Henry | A61M 16/0683 |
| | | | | 128/207.11 |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2013/0074845 | A1* | 3/2013 | Smith | A61M 16/0616 |
| | | | | 128/205.25 |

FOREIGN PATENT DOCUMENTS

| | | | |
|---|---|---|---|
| WO | WO 2000/078381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | WO 2009/052560 | A1 | 4/2009 |
| WO | WO 2010/135785 | A1 | 12/2010 |
| WO | WO 2012/171072 | A1 | 12/2012 |
| WO | WO 2013/020167 | A1 | 2/2013 |

OTHER PUBLICATIONS

Extended European Search Report mailed Feb. 13, 2023 in European Application No. 22196231.9, 7 pages.

* cited by examiner

Nasal cavity

Oral cavity

Larynx

Vocal folds

Oesophagus

Trachea

Bronchus

Lung

Heart

Diaphragm

Alveolar sacs

Nasal cavity

Nasal bone

Lateral nasal cartilage

Greater alar cartilage

Nostril

Lip superior

Lip inferior

Hard palate

Soft palate

Oropharynx

Tongue

Epiglottis

Vocal folds

Esophagus

Trachea

Larynx

Coronal plane

Superior

Posterior

Anterior

Inferior

Frankfort horizontal

Nasolabial angle

Sagittal plane

Pronasale columella

Subnasale

Naris

Major axis
of naris

Upper vermilion

Lip inferior

Naso-labial sulcus

Frontal sinus

Nasal bone

Septum cartilage

Medial crus of greater alar cartilage

Anterior nasal spine

Frontal process of maxilla

Lesser alar cartilage

Fibrofatty tissue

Epidermis

Adipose tissue

Nasal bone

Lateral cartilage

Septum cartilage

Greater alar cartilage

Parietal bone

Temporal bone

Occipital bone

Trapezius m.

Frontal bone

Sphenoid bone

Nasal bone

Zygomatic bone

Maxilla

Masseter m.

Mandible

Mental protuberance

Digastricus m.

Sternocleidomastoid m.

Concha

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

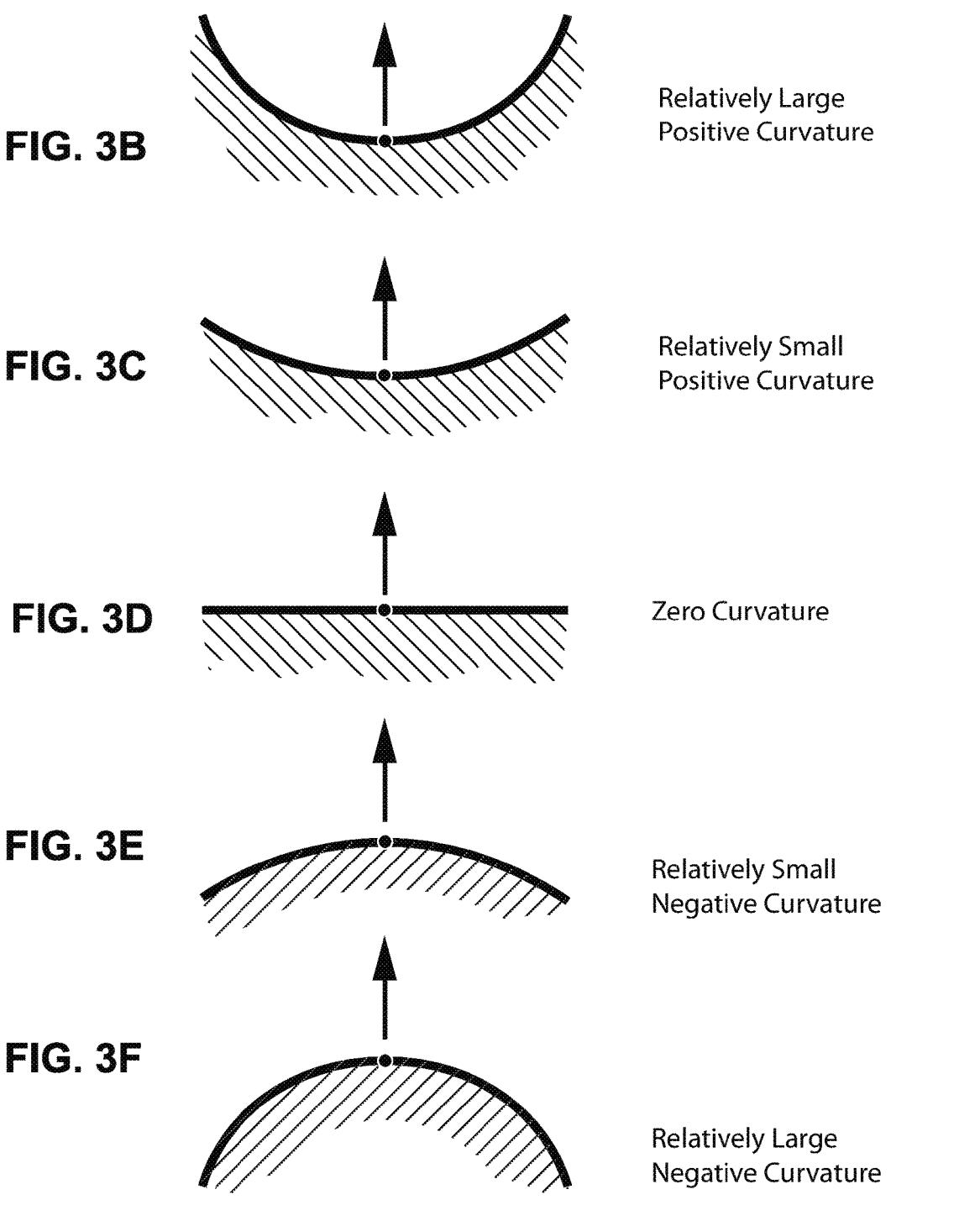
FIG. 3B    Relatively Large Positive Curvature
FIG. 3C    Relatively Small Positive Curvature
FIG. 3D    Zero Curvature
FIG. 3E    Relatively Small Negative Curvature
FIG. 3F    Relatively Large Negative Curvature

Curve

FIG. 3I

Surface

Surface

Interior surface

Interior
surface

Left-hand rule
Binormal(B)
Osculating plane
Tangent(T)
Normal(N)
FIG. 3O
Right-hand rule
Binormal(B)
Osculating plane
Tangent(T)
Normal(N)
FIG. 3P
Left ear helix
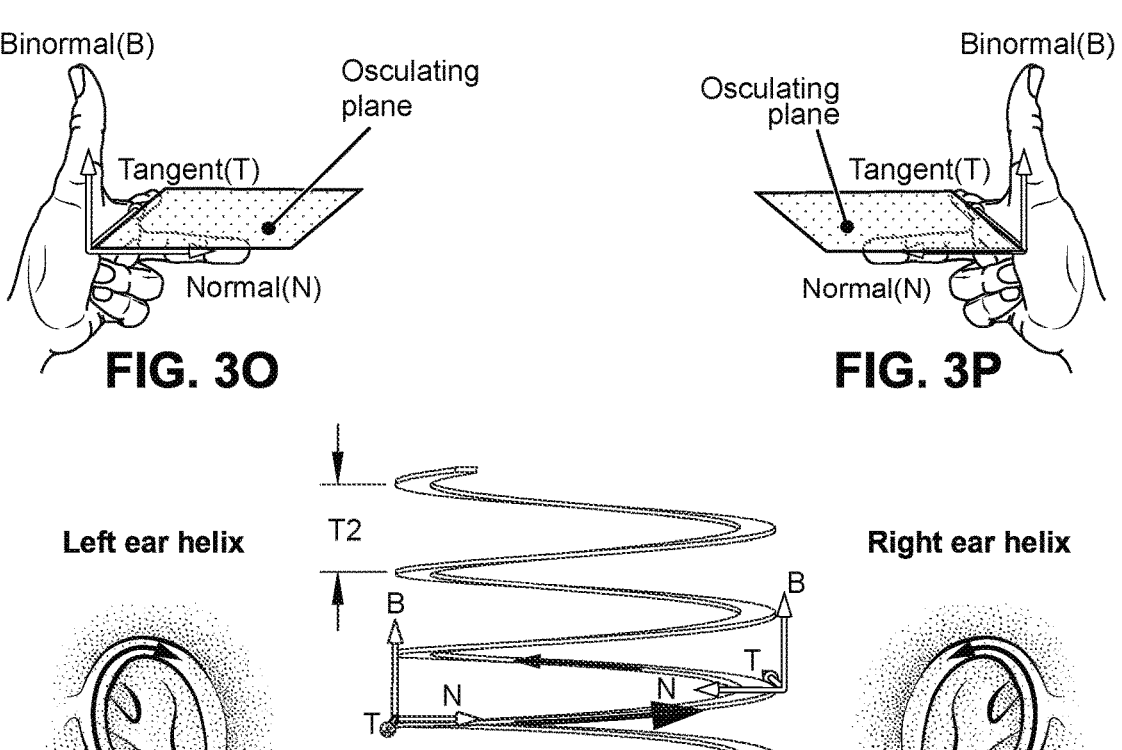
FIG. 3Q
T2
B
T
N
N
T
B
T1
Right-hand helix
Right-hand positive
FIG. 3S
Right ear helix
FIG. 3R
Right-hand negative
(=left-hand positive)
Right-hand positive
Right-hand negative
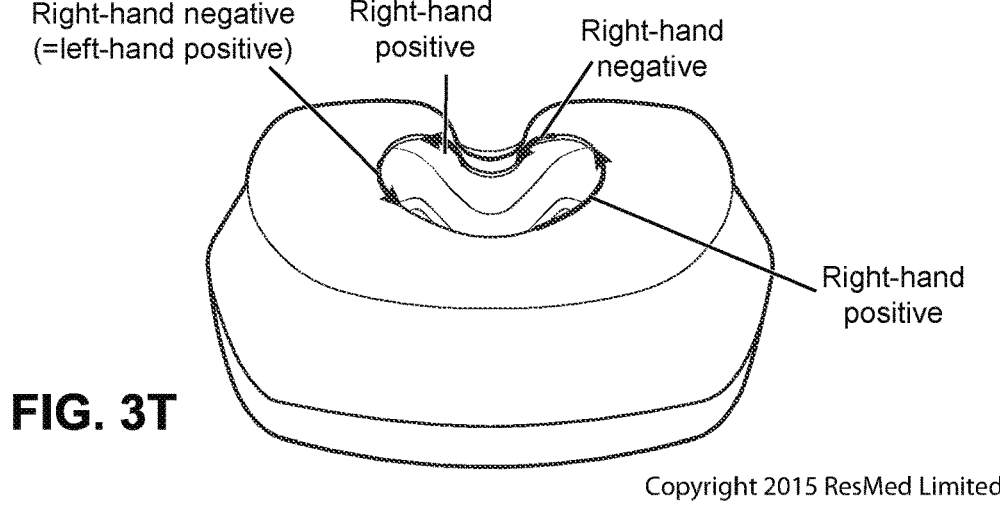
Right-hand positive
FIG. 3T 3350     3372

3355

3357

3377

3378A

3380

Pull

3378B

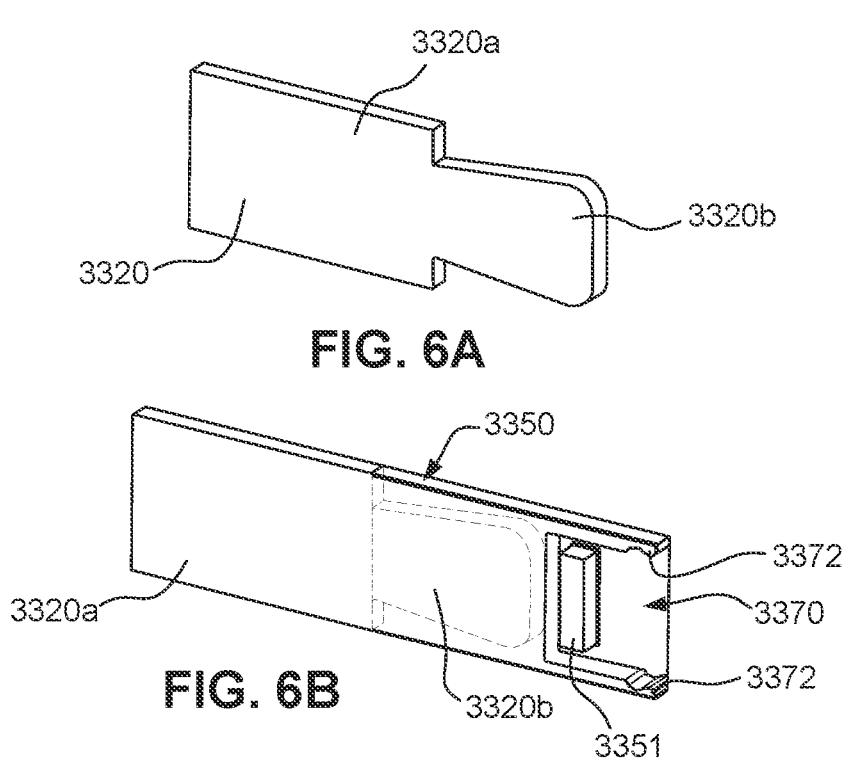
FIG. 6A
FIG. 6B
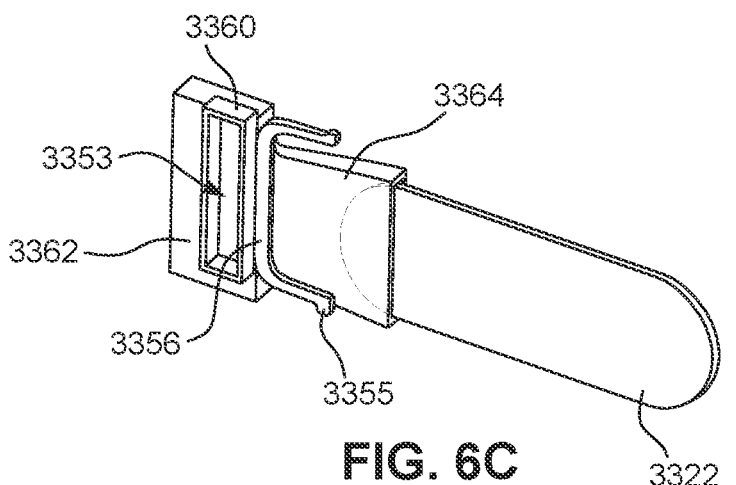
FIG. 6C
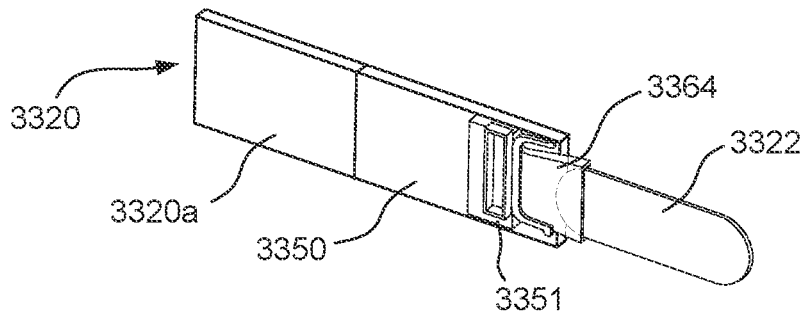
FIG. 6D

HEADGEAR WITH TENSION LIMIT DETECTION FEATURE

1 CROSS-REFERENCE TO RELATED APPLICATIONS

This application claims the benefit of Singaporean Patent Application No. 10202110289T, filed Sep. 17, 2021, the entire contents of which is hereby incorporated by reference in its entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

A problem that can arise in relation to respiratory therapy is that there may be a tendency to over-tighten the patient interface to ensure a tight seal between the mask and the patient's face. As the patient interface is worn for long periods, this may result in formation of pressure sores, particularly in older patients who tend to have thinner and dryer skin that is more susceptible to damage. This is estimated to occur in 10%-30% of patients. The degree of tightening that is needed for a therapeutically effective seal can be subjective, and prone to human error.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface comprising a seal-forming structure, a plenum chamber, and a positioning and stabilising structure.

One form of the present technology comprises a headgear for use with a patient interface wherein the headgear includes a tension limiting device configured to alert the patient to over tensioning in the headgear.

One form of the present technology comprises a headgear for use with a patient interface wherein the headgear includes a tension control feature configured to limit the amount of tension that a patient applies to the headgear.

One form of the present technology comprises a headgear for use with a patient interface wherein the headgear includes a first position and a second position with a greater length than the first position. Moving from the first position to the second position produces a signal (e.g., an audible sound) observable by the patient (and/or another person).

One form of the present technology comprises a patient interface comprising a seal-forming structure configured to form a seal on the patient's face and a headgear configured to maintain the seal-forming structure in a sealed position, wherein the headgear is configured to output a signal as a result of an overtightened condition.

In some forms, the signal may be auditory, visual, and/or tactile.

One form of the present technology comprises a headgear for a patient interface, the headgear comprising one or more straps each having a first end for connecting to a mask; wherein the first end of each strap comprises, a connection portion, the connection portion being grippable by a user to pull the strap to increase a tension in the strap, a first rigid member, and a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance; wherein the resilient carrier is constructed and arranged such that the threshold distance corresponds to a desired tension limit for the strap.

In another form of the present technology, the first rigid member comprises a channel within which the second rigid member is slidingly movable.

In another form of the present technology, the at least part of the second rigid member comprises a projection located at an end of a cantilever arm.

In another form of the present technology, the second rigid member is a C-clip.

In another form of the present technology, the resilient carrier comprises an elastomer.

In another form of the present technology, the resilient carrier is dimensioned to provide the desired tension limit, and/or is formed from a material having a Shore hardness that provides the desired tension limit.

In another form of the present technology, the second rigid member is at least partly embedded in the resilient carrier.

In another form of the present technology, the resilient carrier is connected to the first rigid member via a rigid interface that is separate from the second rigid member.

In another form of the present technology, the rigid interface is embedded in the resilient carrier.

In another form of the present technology, the one or more straps comprise at least one top strap and at least one bottom strap, and wherein a desired tension limit for the at least one top strap is different than a desired tension limit for the at least one bottom strap.

In another form of the present technology, the connection portion is a hook tab.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

In one aspect, a method comprises connecting a first rigid member and a second rigid member of a headgear together in order to allow relative movement between the first and second rigid members.

In one aspect, a method comprises cutting a strip of material into a shape of a strap; connecting the strip of material to a first rigid member; connecting a second rigid member to the first rigid member to form a continuous strap; wherein connecting the second rigid member to the first rigid member is configured to allow relative movement between the first and second rigid members.

In some forms, a) the cutting is accomplished using ultrasonic or radio frequency cutting; b) cutting further comprises creating a first portion with a first width and a second portion with a second width smaller than the first width; c) connecting the strip of material to a first rigid member further includes overmolding the first rigid member to the strip of material; d) overmolding occurs on the second width and not on the first width.

In some forms, a) connecting the second rigid member to a resilient carrier; b) the resilient carrier directly connected to the first rigid member and connecting the second rigid member to the first rigid member; c) the resilient carrier includes a base connected to one side of the second rigid member and a tongue connected to the other side of the first rigid member.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1:
Figure 2A:
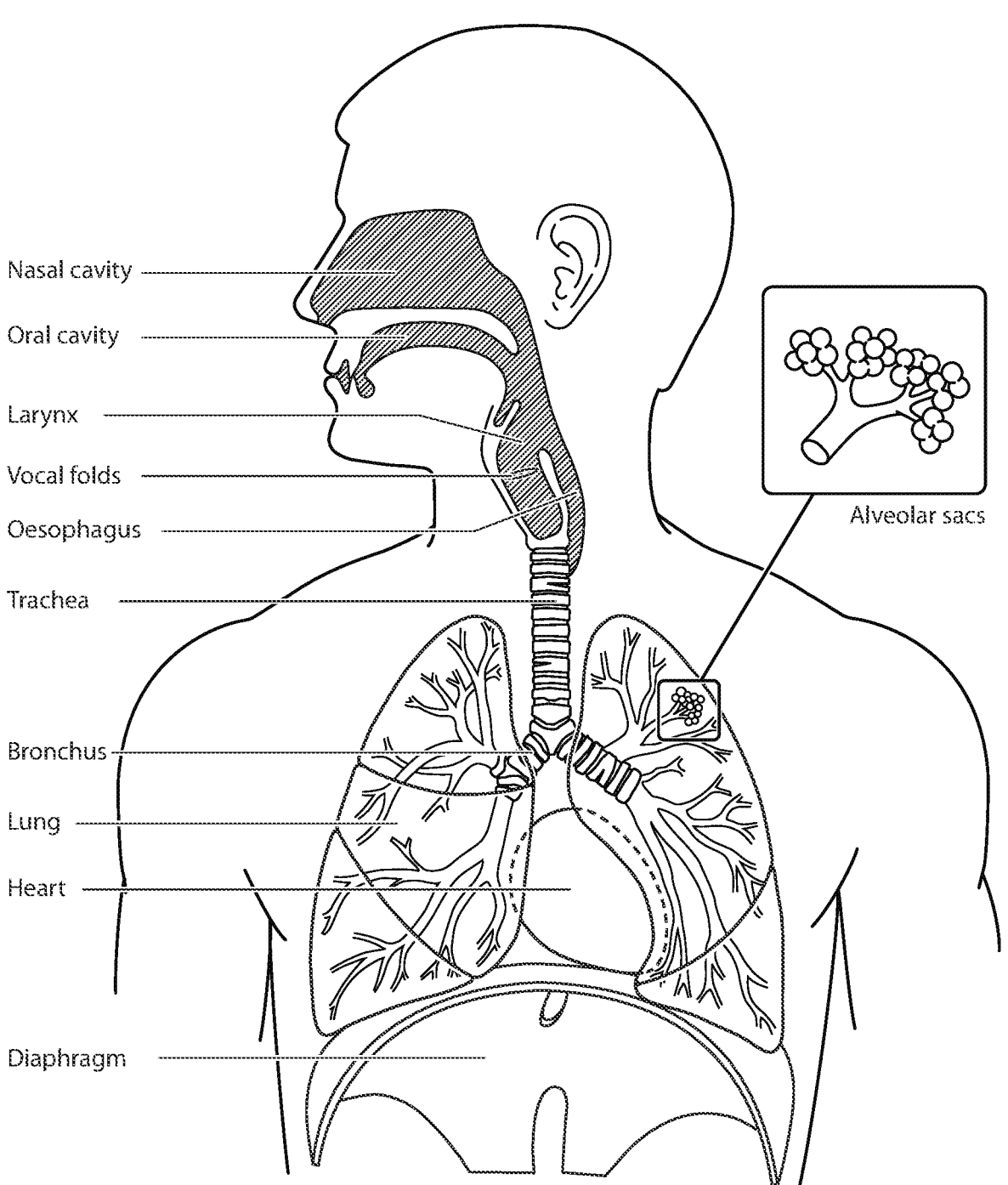
FIG. 2A shows an overview of a human respiratory system including the nasal and oral cavities, the larynx, vocal folds, oesophagus, trachea, bronchus, lung, alveolar sacs, heart and diaphragm.
Figure 2B:
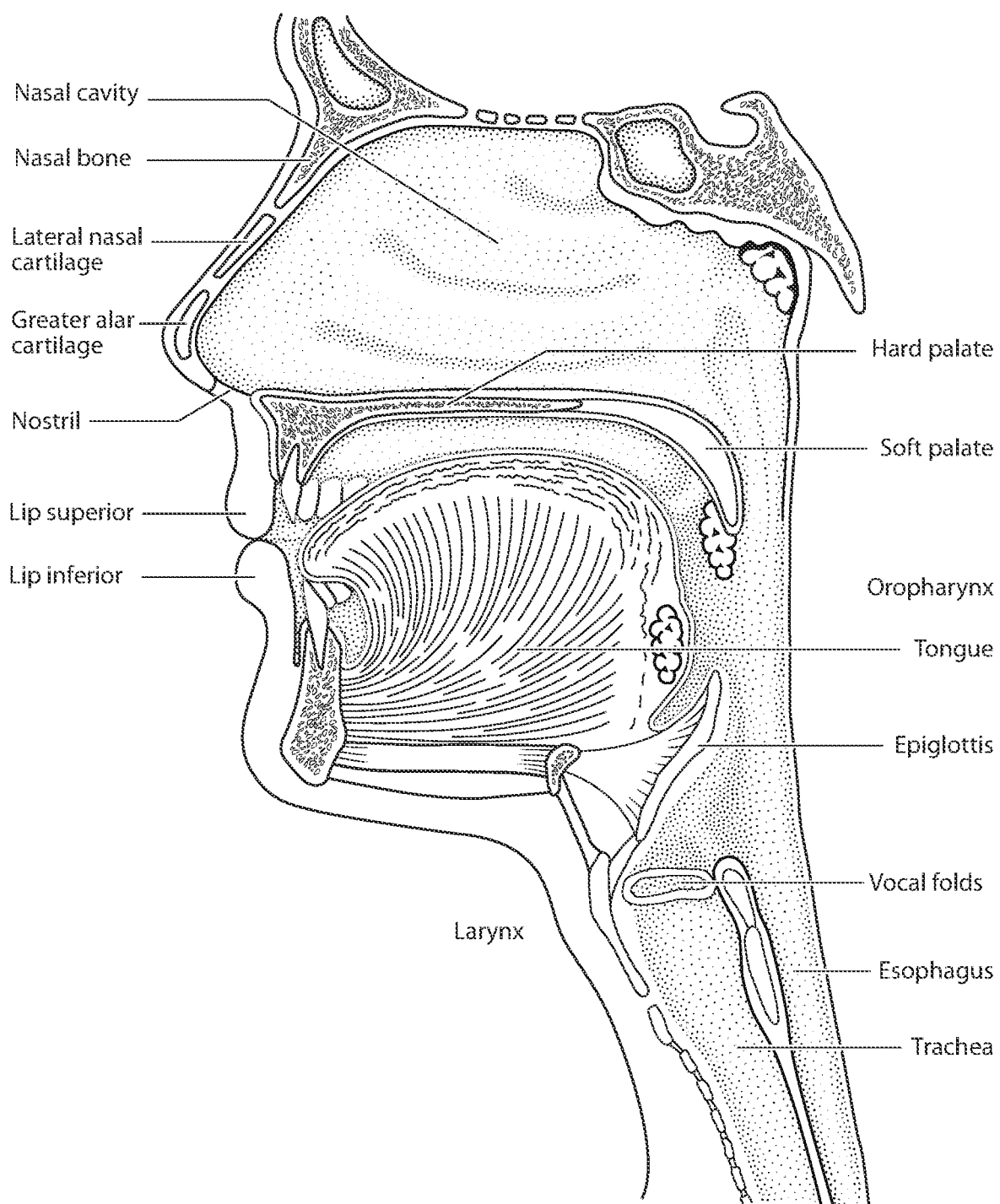
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
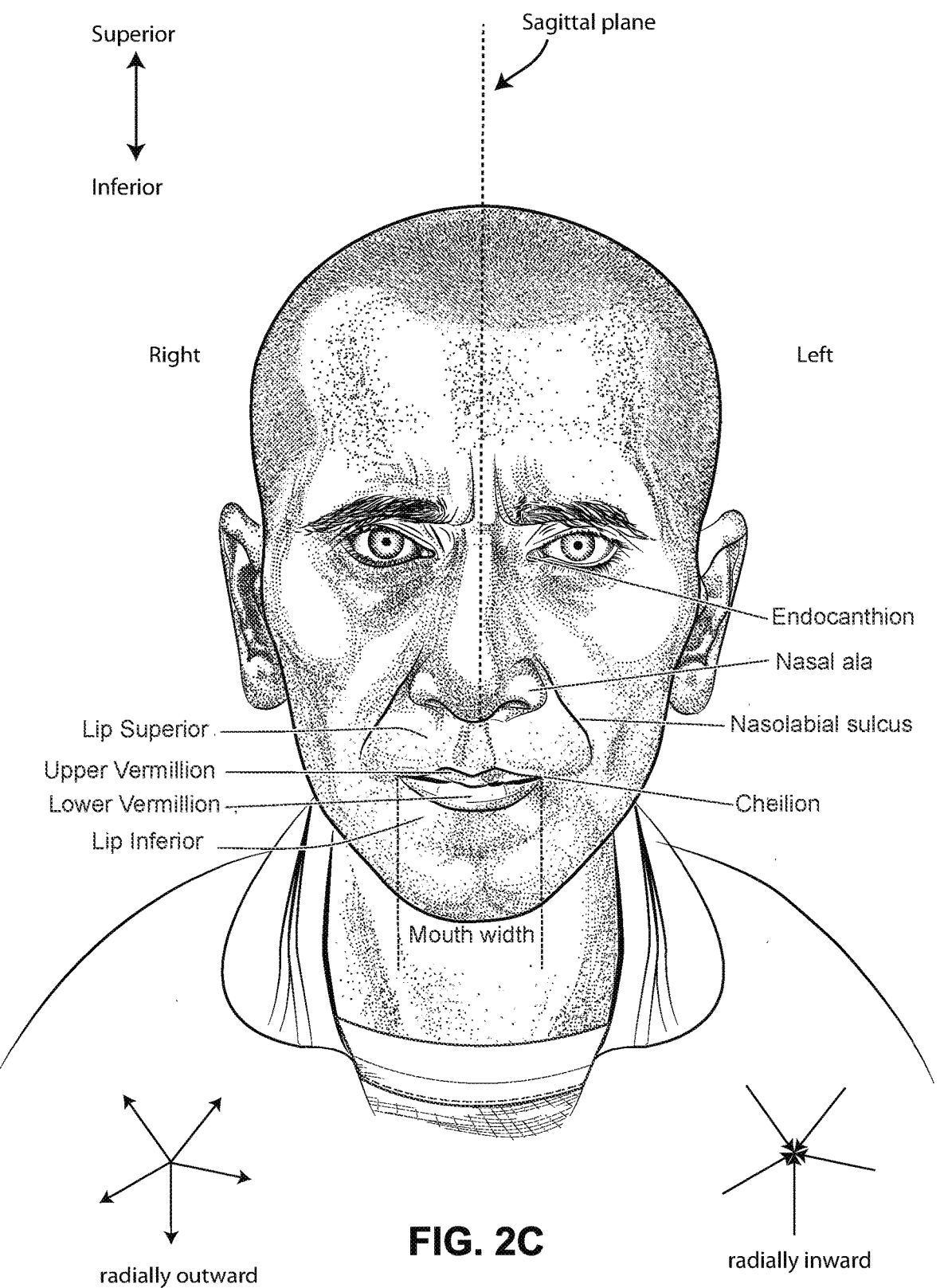
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
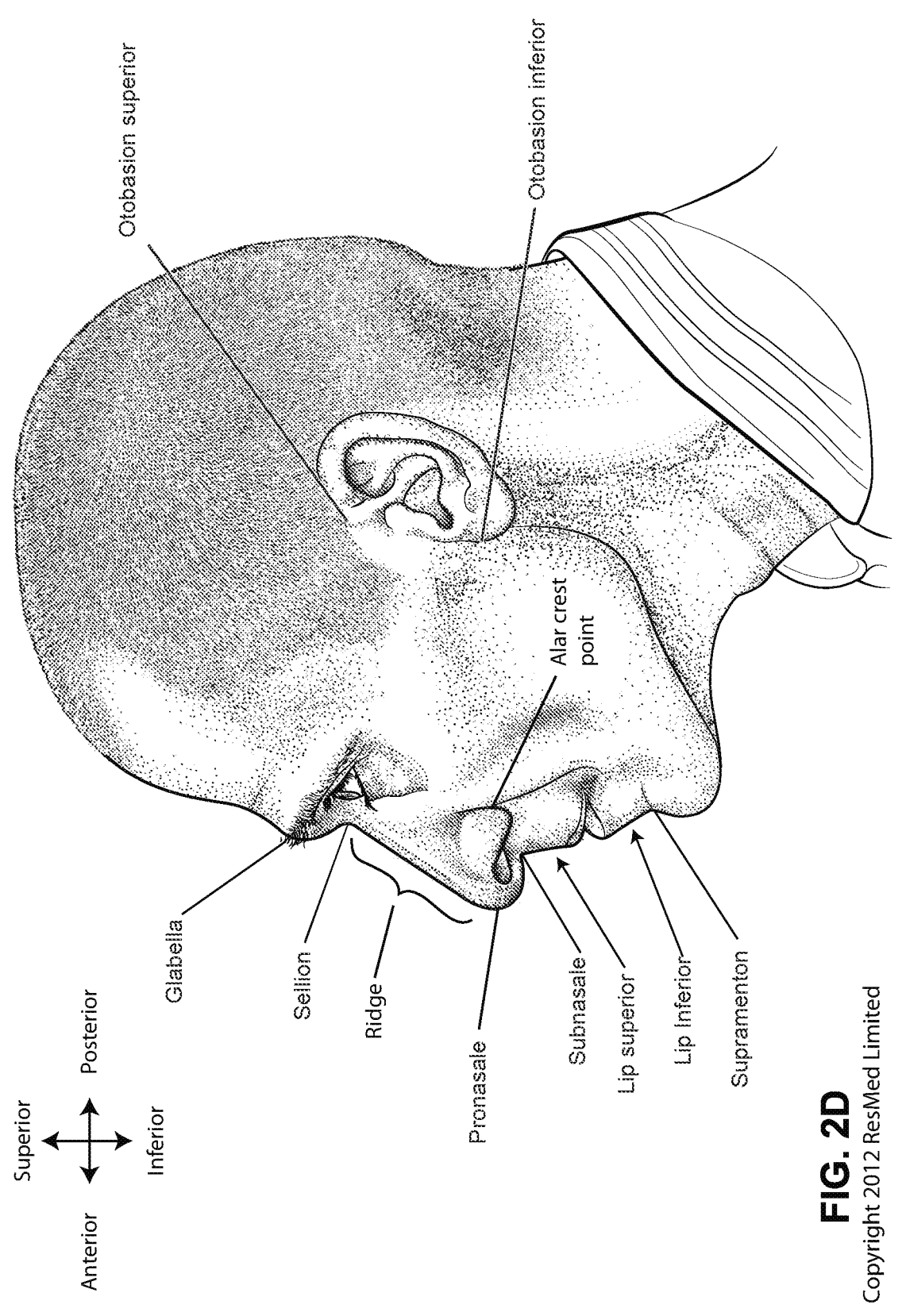
FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
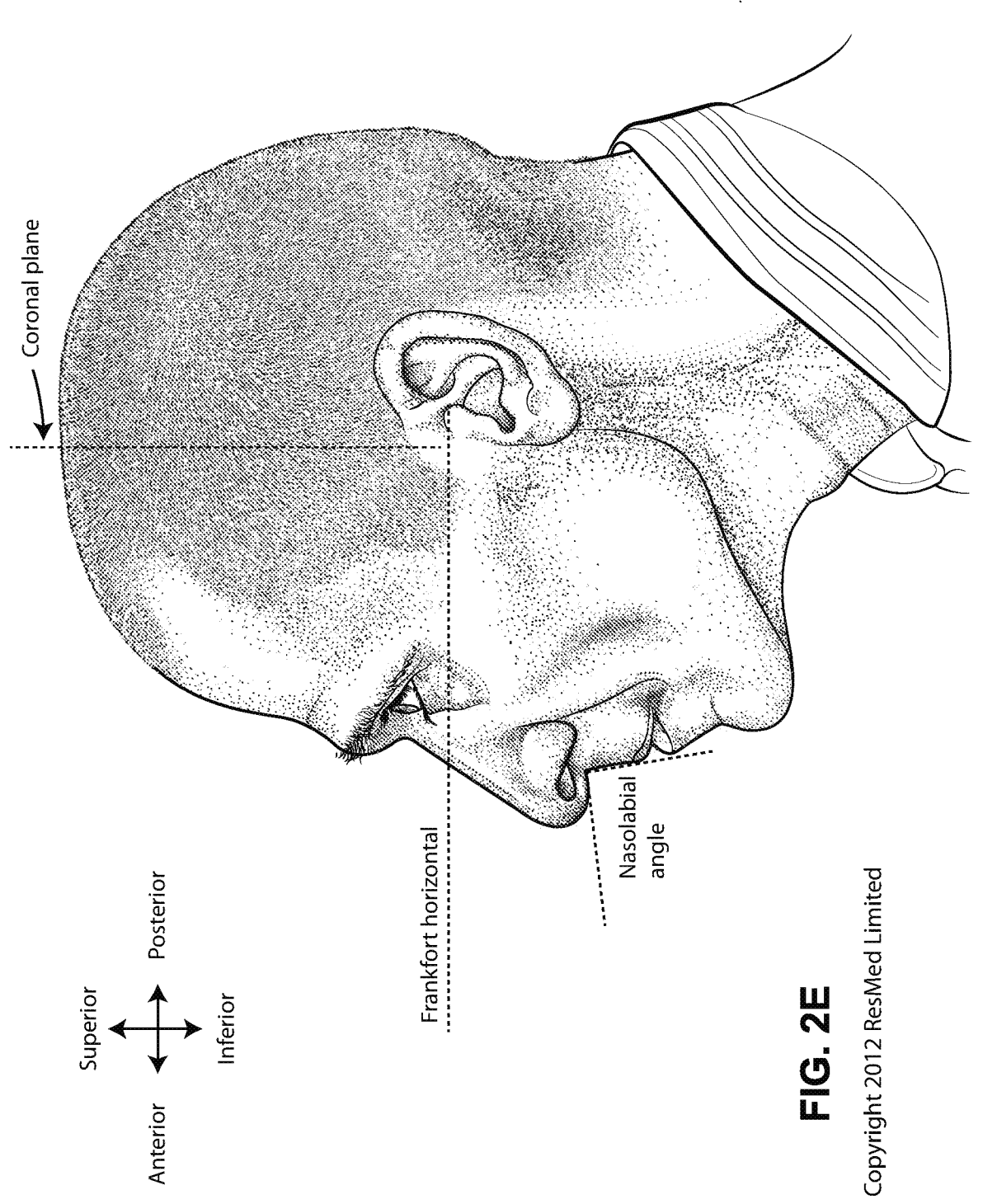

FIG. 2E is a further side view of a head. The approximate locations of the Frankfort horizontal and nasolabial angle are indicated. The coronal plane is also indicated.

Figure 2F:
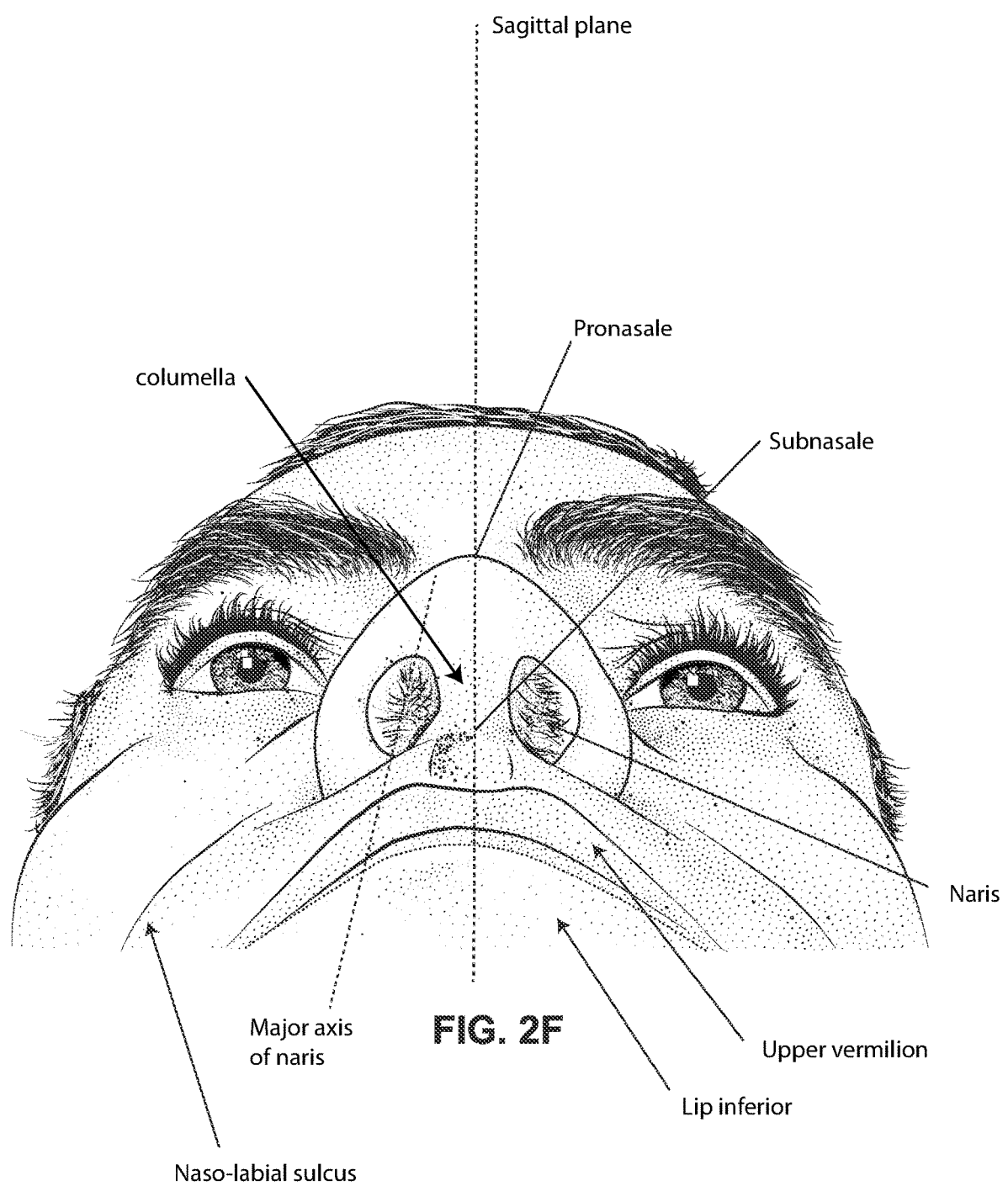

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
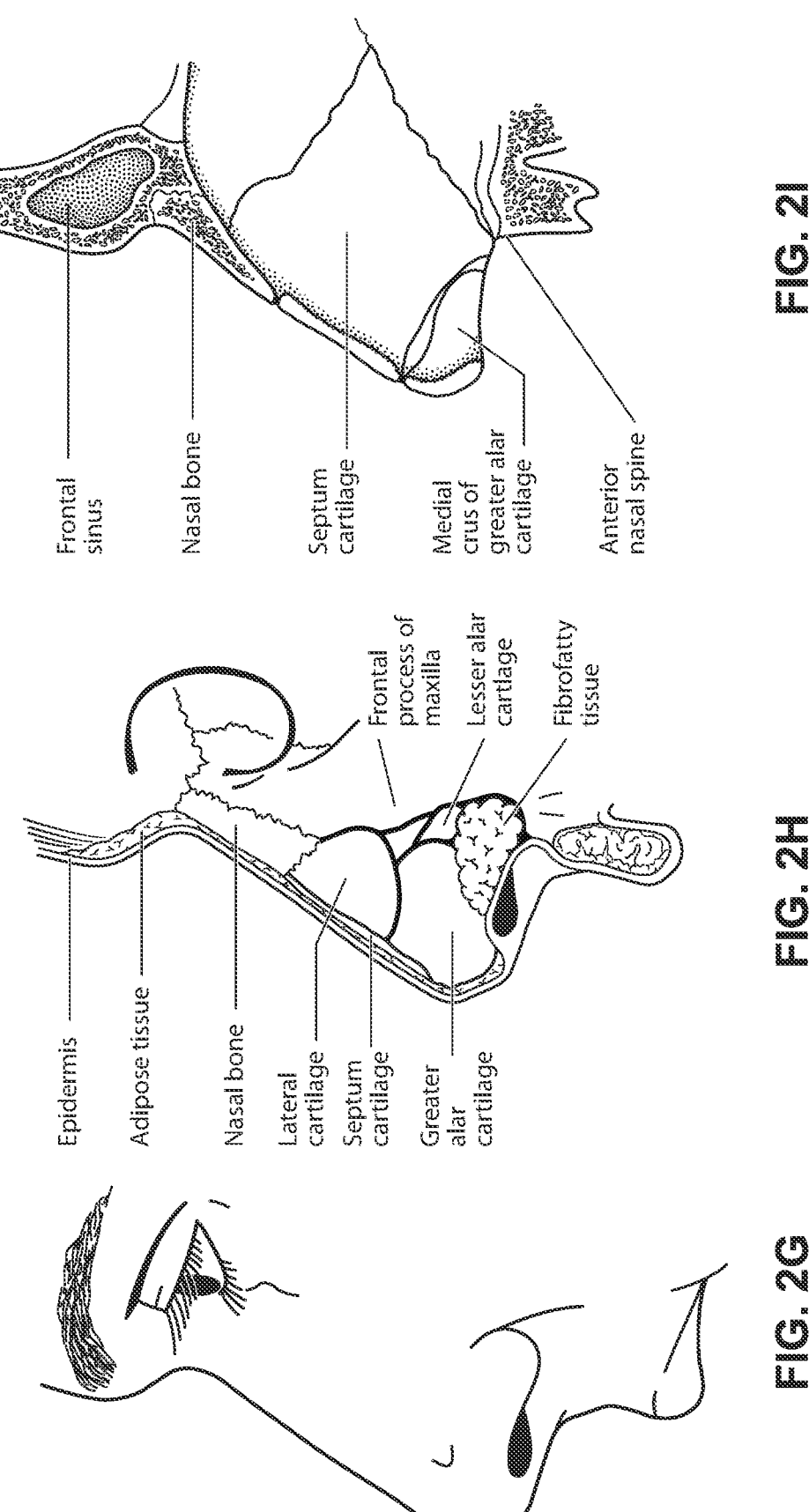

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
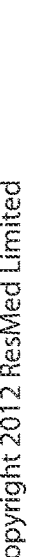

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
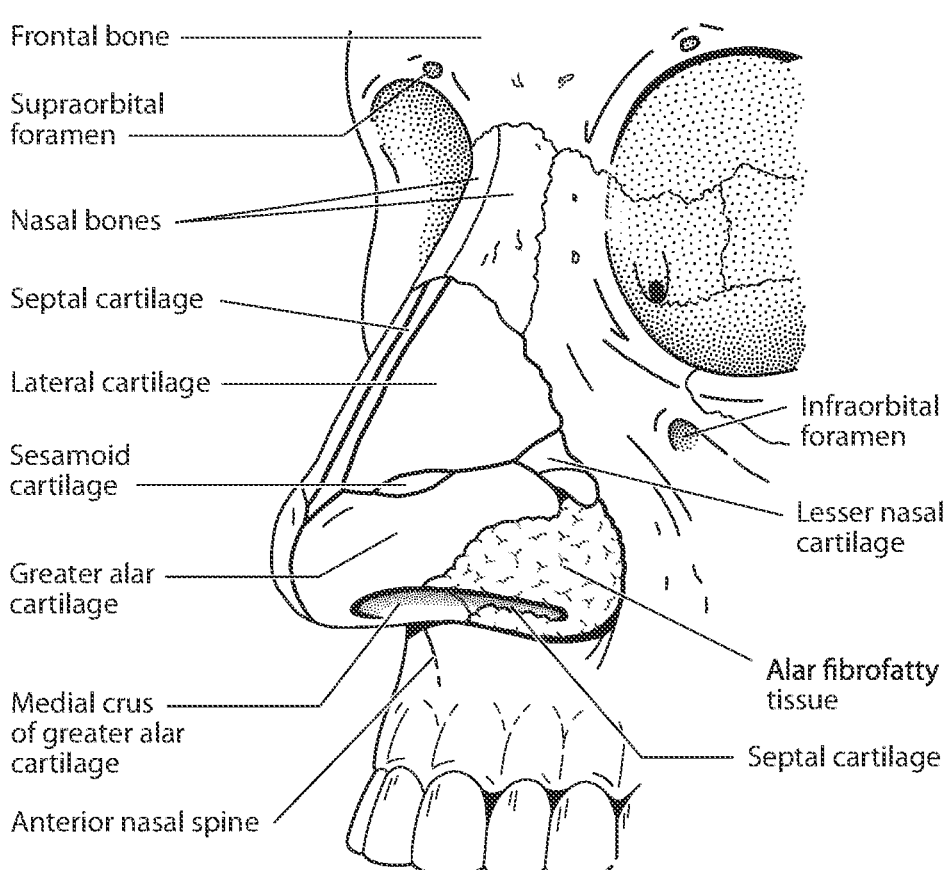

FIG. 2L shows an anterolateral view of a nose.

4.3 Patient Interface

Figure 3A:
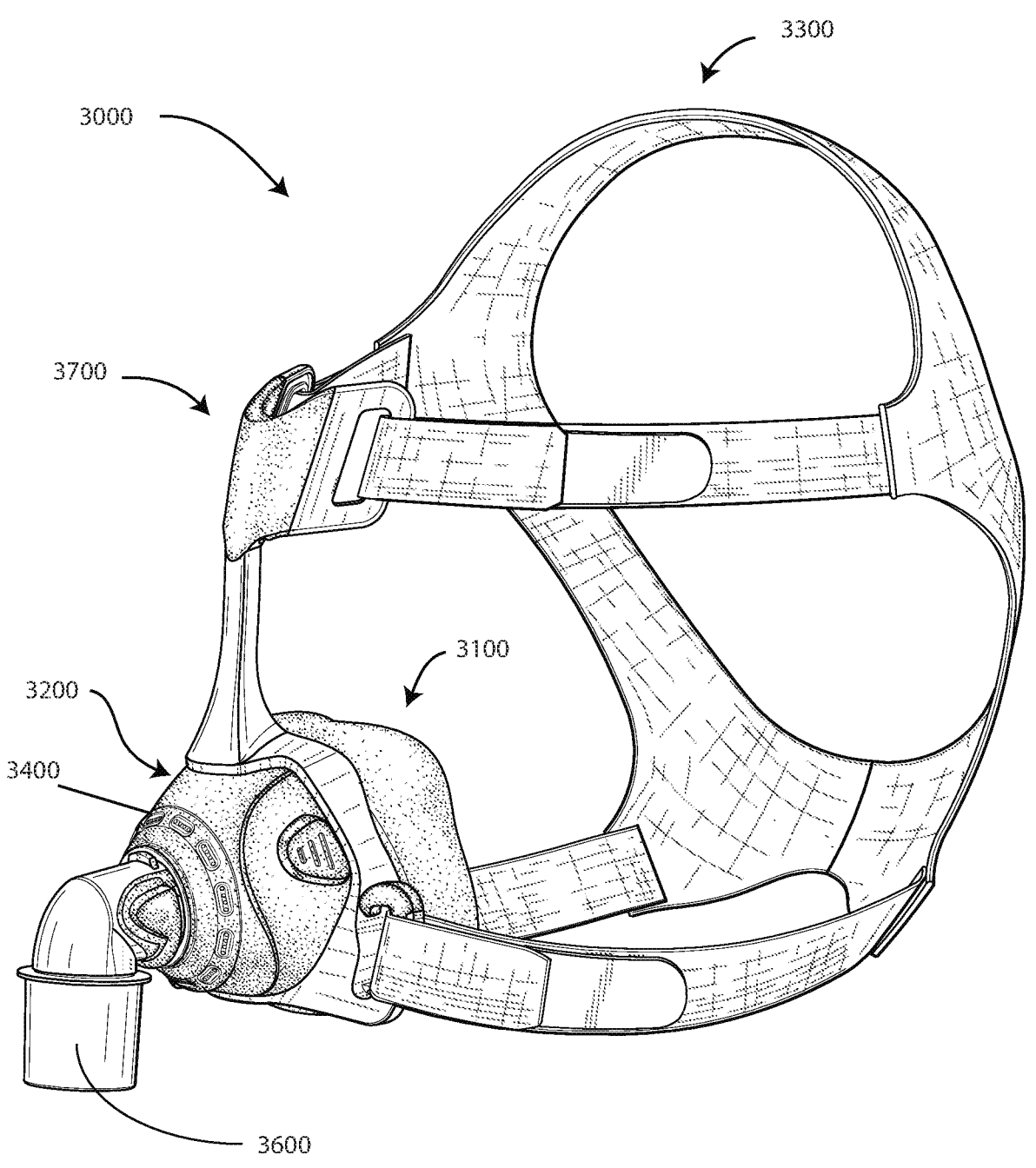

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
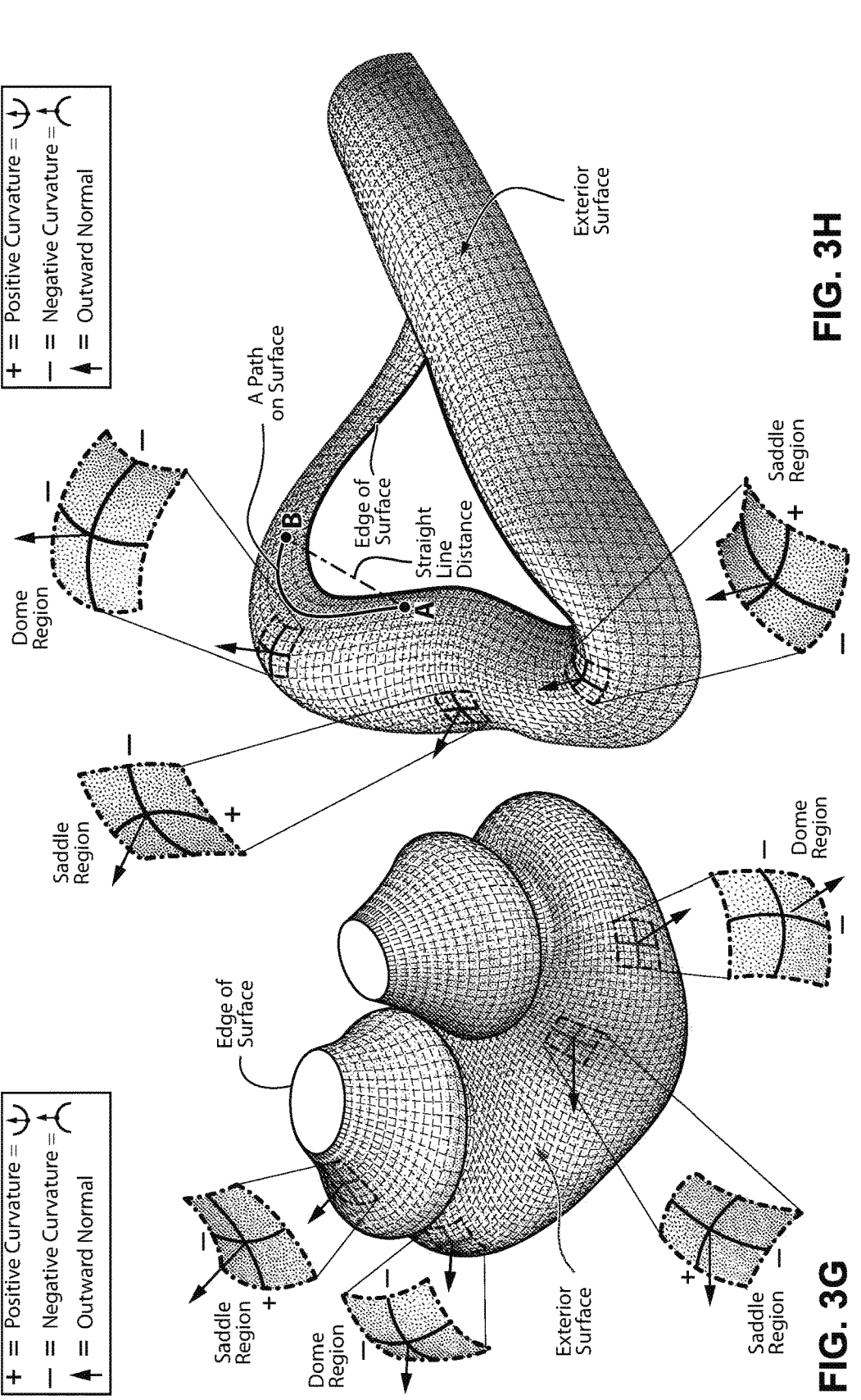

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figures 3I, 3J, 3K, 3L, 3M, 3N:
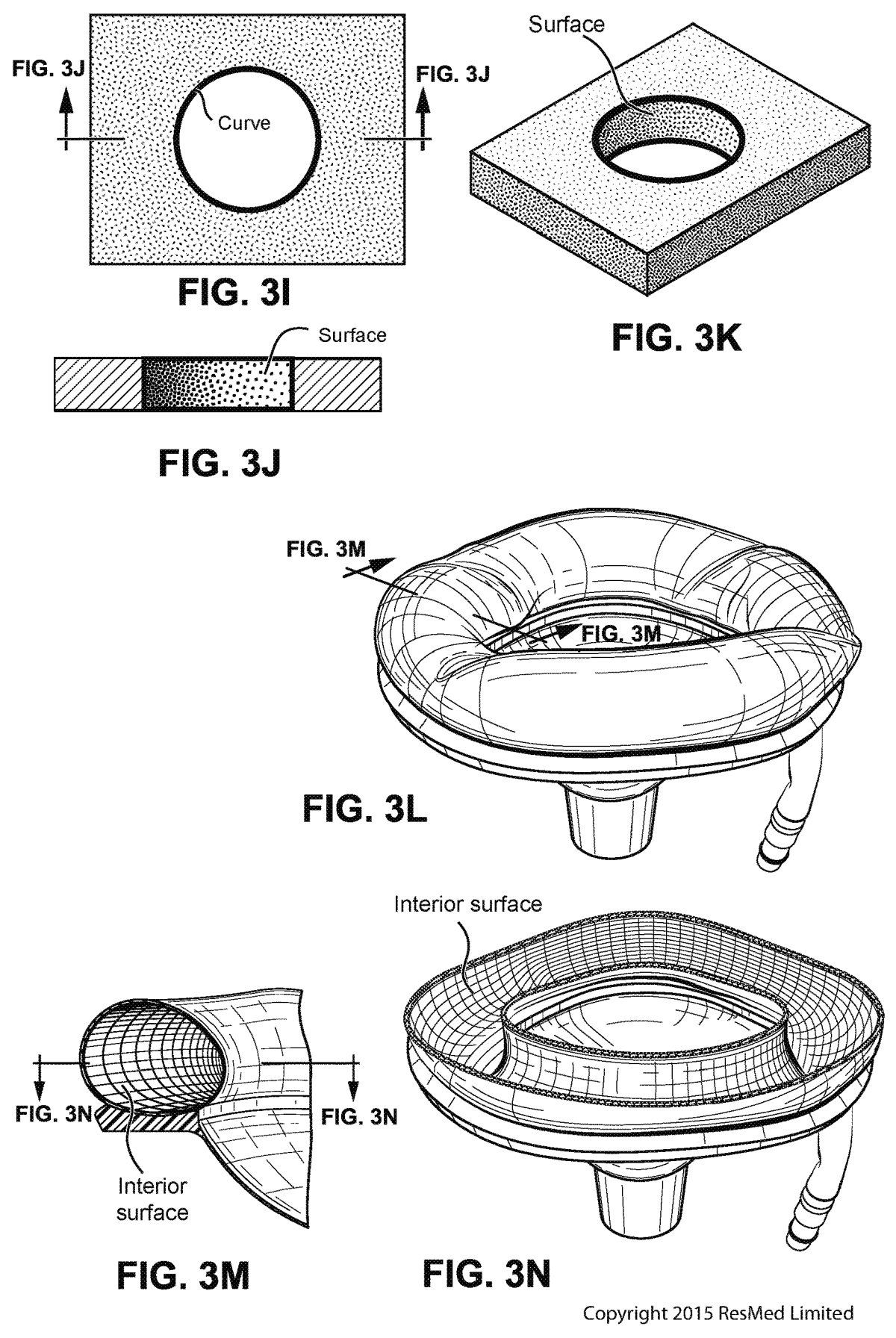

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
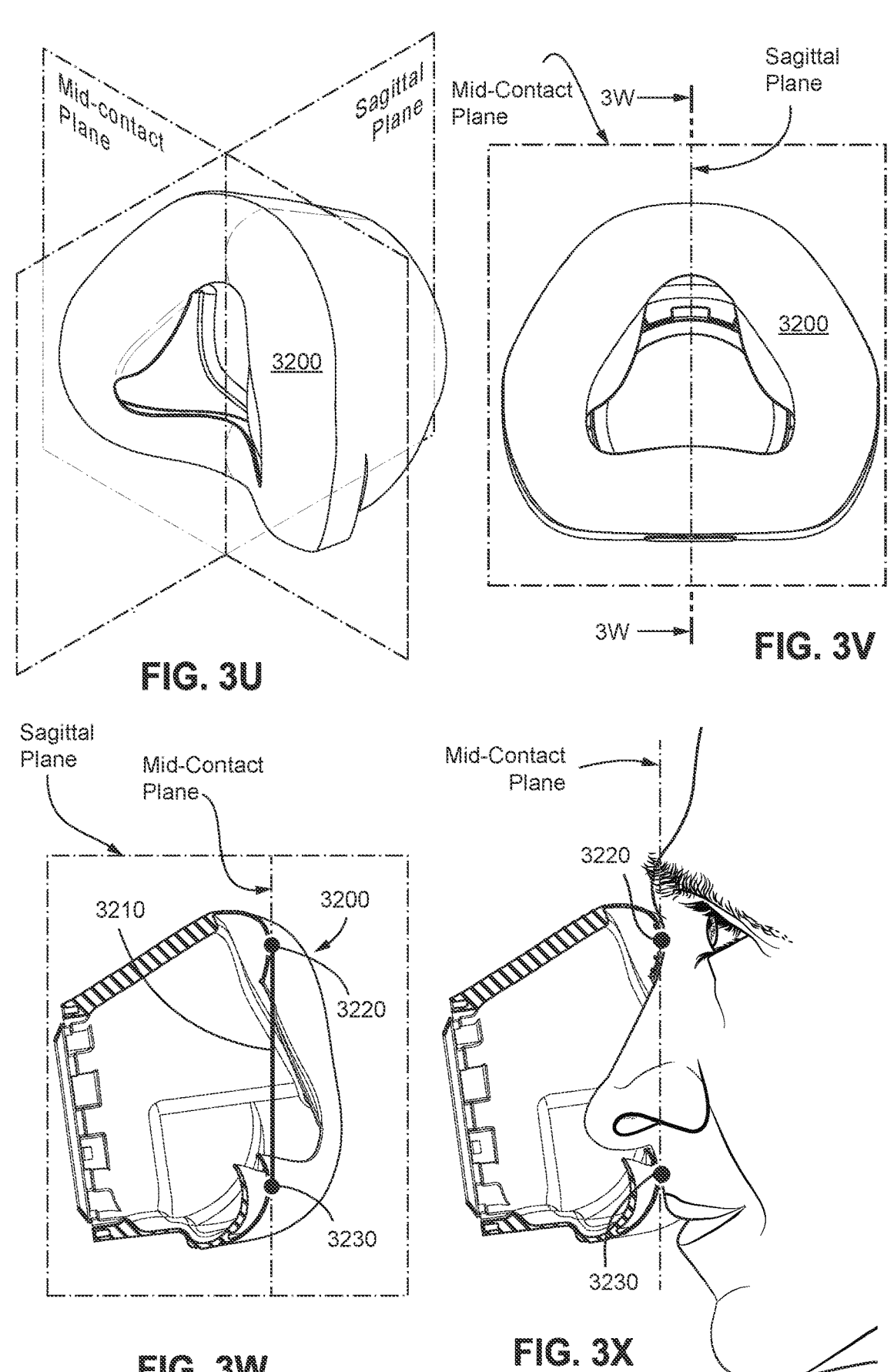

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 4:
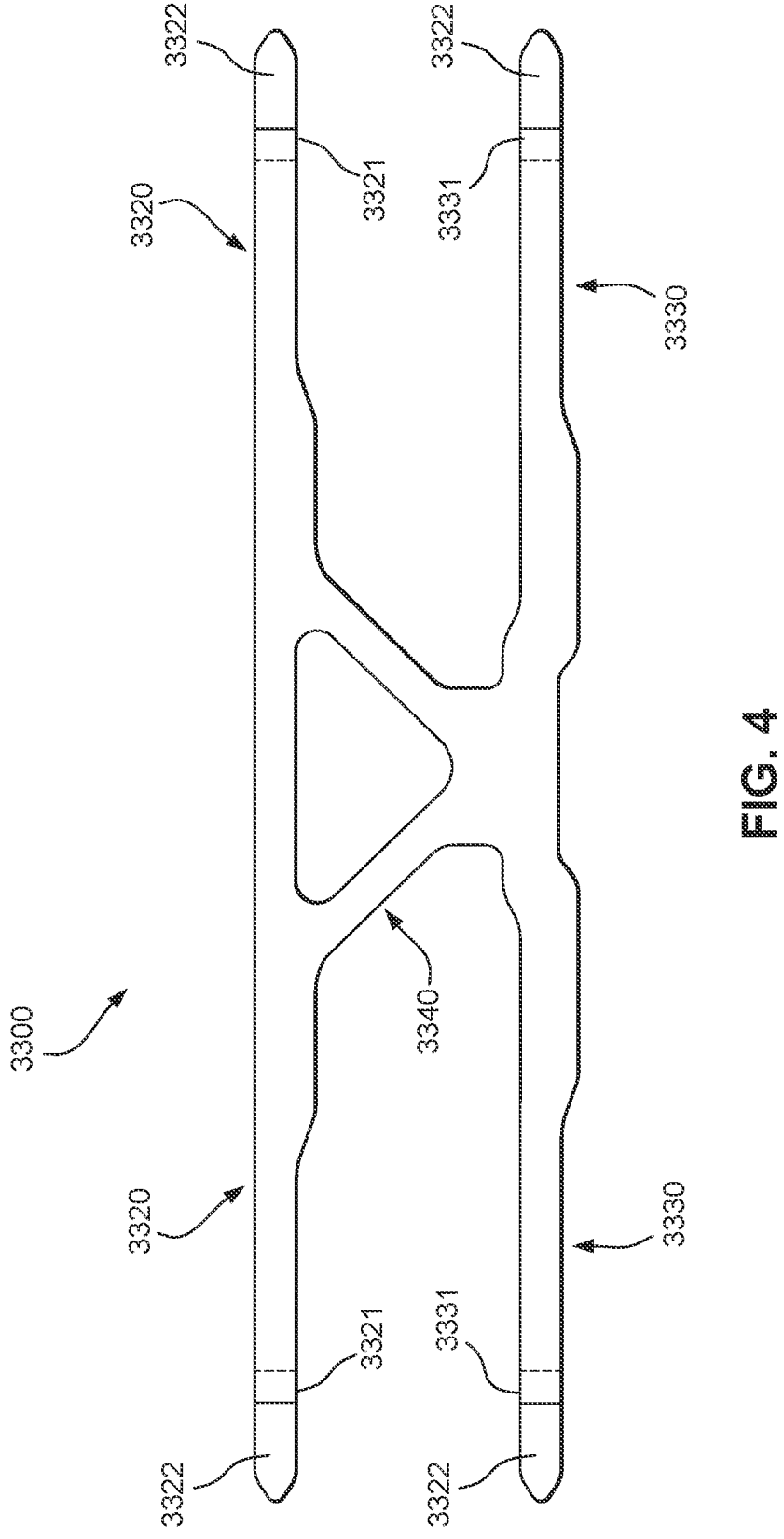

FIG. 4 shows headgear in accordance with one form of the present technology, in flattened form.

Figure 5A:
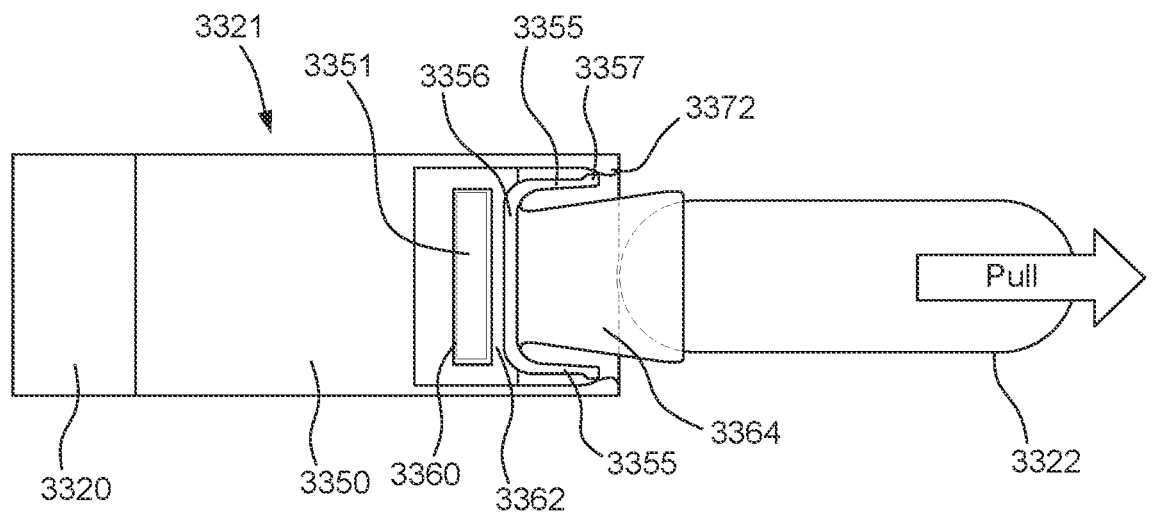

FIG. 5A shows a schematic view of an end portion of a strap of the headgear of FIG. 4.

Figure 5B:
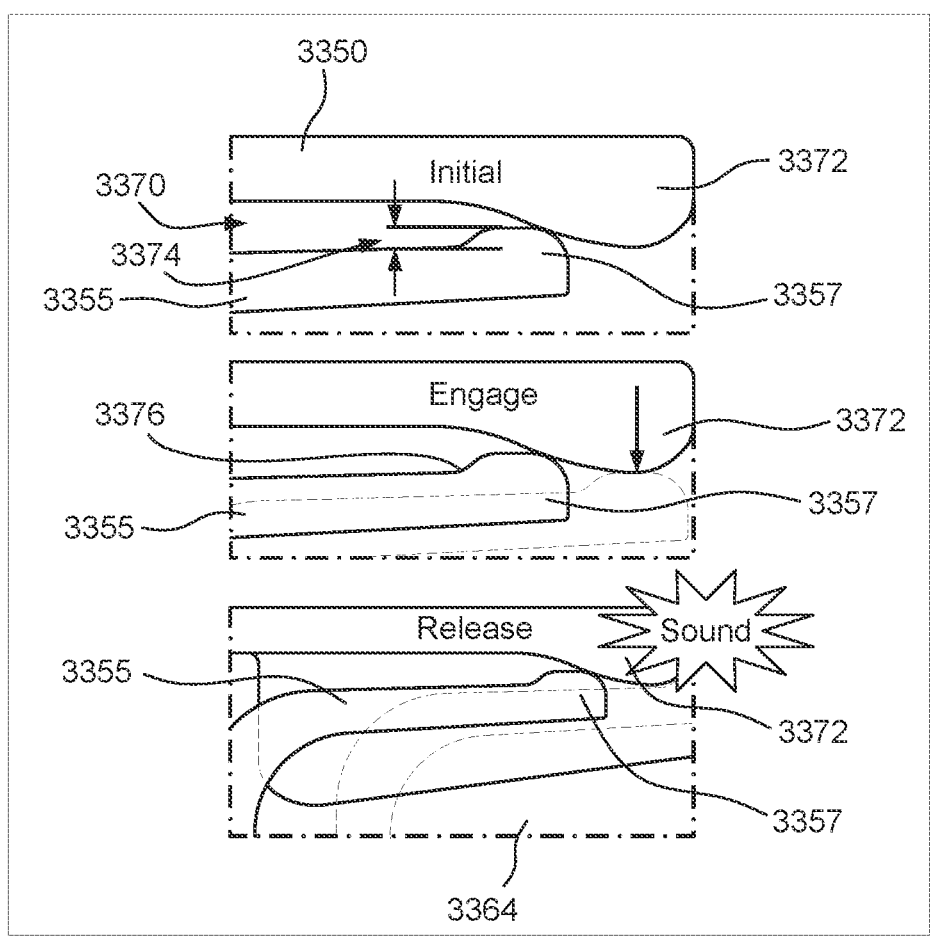

FIG. 5B is a schematic series of views showing operation of a tension limit detection feature of the strap of FIG. 5A.

Figures 5C, 5D:
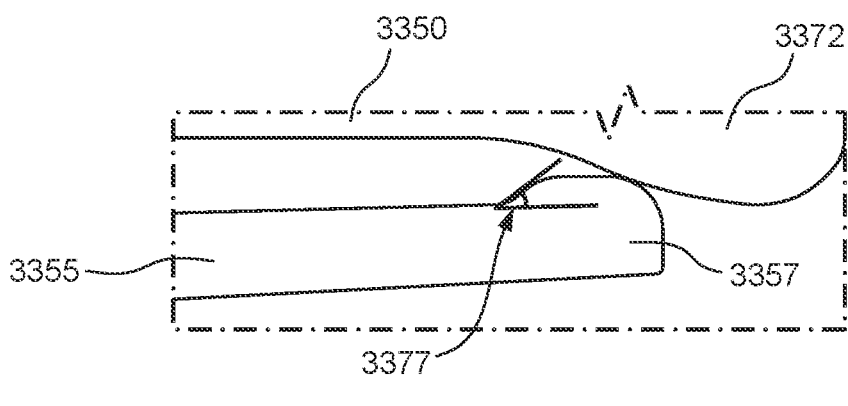

FIG. 5C is an enlarged view of a protrusion of the strap of FIG. 5A.

FIG. 5D is a schematic view showing the elastic deformation of the strap of FIG. 5A.

FIGS. 6A to 6D show various stages of manufacture of a headgear strap in accordance with one form of the present technology.

FIGS. 7A to 7D show various forms of patient interface for which headgear straps having a tension limit detection feature are suitable.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure (also referred to herein as headgear) 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure (headgear) 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Tension Limit Detection Feature

FIG. 4 shows an example of headgear 3300, which may, for example, be used as part of the patient interface 3000 of FIG. 3A. The headgear 3300 may be one example of the positioning and stablising structure. The headgear 3300 may be constructed from a composite of textile material, polyurethane foam, and/or loop material and hook material, and the headgear 3300 may include a pair of upper straps 3320 and lower straps 3330 and a generally triangular back portion 3340. In the illustrated example, the triangular back portion 3340 may be an opening formed between several straps of the headgear 3300, although the triangular back portion 3340 may also include complete material coverage (e.g., so that the patient's head is not exposed through the triangular back portion 3340 while in use). The back portion 3340 may also be another shape (e.g., circular, elliptical, rectangular, etc.) instead of triangular. A piece of hook material 3322 (e.g., such as Velcro®), also referred to herein as a hook tab, is attached to the end of each of the four straps so that the straps may be secured to and/or through attachment points on the mask 3200, or to another structure that supports the mask 3200 (see FIG. 3A).

The hook material 3322 may be 'one way' hook material so that it does not catch on itself in the process of overlaying the straps before they are brought into engagement.

In other, unillustrated, arrangements, the straps 3320, 3330 may be adapted to fit to a male clip connector which clips into a female connector moulded into a mask frame of mask 3200. In other, unillustrated examples, the connection portion of each strap 3320, 3330 may include one of a male and female connector for connecting to a cooperating female or male connector on the mask 3200. The male or female connector on the straps 3320, 3330 may be used in place of the hook material 3322, or in addition to the hook material 3322. In still further unillustrated examples, the connection portion of each strap 3320, 3330 may include a magnet for connecting to a separate magnet on the mask and/or on another portion of the respective strap 3320, 3330. In a still further unillustrated embodiment, the connection portion of each strap 3320, 3330 may include both a magnet and a mechanical fastener.

Each of the straps 3320, 3330 may comprise a main portion formed from a fabric/foam/fabric laminate, and a first end (respectively, 3321 for the upper straps 3320 and 3331 for the lower straps 3330) for connecting to the mask 3200 (e.g., either directly or via an intermediate structure, like a frame).

Straps 3320, 3330 of headgear 3300 may each comprise a tension limit detection feature. The feature may indicate when a predetermined tension limit in the straps 3320, 3330 has been exceeded. This feature may be a visual indicator, an auditory indicator, and/or a tactile indicator that may alert the patient and/or others that the headgear 3300 is too tight. The patient may then loosen the headgear 3300 and/or choose a different sized headgear 3300.

As best shown in FIG. 5A, an end portion 3321 of each of the upper straps 3320 comprises a connection portion, in the form of hook tab 3322, that may be gripped by a user to pull the strap 3320 to tighten (e.g., to increase tension in) the strap. The end portion 3321 comprises a first rigid member 3350 and a second rigid member (formed by 3355, 3356, 3357) that extends from a resilient carrier (3362, 3364) that is connected to the hook tab 3322.

In the illustrated form of the technology, the second rigid member is a C-clip structure that comprises a pair of cantilever arms 3355 joined by a web 3356. The second rigid member may be at least partly embedded in the resilient carrier. For example, at least the web 3356 may be embedded in the resilient carrier with the cantilever arms 3355 being exposed.

As illustrated in FIG. 5A (as well as FIG. 6C), the web 3356 may be connected between the base 3362 and the tongue 3364 that make up the resilient carrier 3362, 3364. This connection may be that the web 3356, and the resilient carrier 3362, 3364 are integrally formed. The web 3356 may extend so that it is longer than at least a portion of the width of the resilient carrier 3362, 3364. For example, the web 3356 may be longer than at least a portion of the width of the tongue 3364. The cantilever arms 3355 may extend from the ends of the web 3356 and be spaced apart from the resilient carrier 3362, 3364.

In some forms, the cantilever arms 3355 and the web 3356 may be formed as an integral piece. Although in other forms, each cantilever arm 3355 may be separately connected to the web 3356.

The second rigid member 3355, 3356 is movable relative to the first rigid member 3350 when the hook tab 3322 is pulled by the user. That is, the second rigid member 3355, 3356 is pulled away from the first rigid member 3350 when the hook tab 3322 is pulled as shown in FIG. 5A. At least part of the second rigid member 3355, 3356 is arranged to strike (or contact) the first rigid member 3350 to cause at least an audible alert when the second rigid member 3355, 3356 travels further than a threshold distance. For example, the second rigid member 3355, 3356 may have a first position that is less than the threshold distance and a second position that is greater than the threshold distance. Moving from the first position to the second position outputs a signal, in this case the audible alert, that is perceived by the patient or another person.

In the example of FIG. 5A, the at least part of the second rigid member 3355, 3356 that is arranged to contact the first rigid member 3350 is a protrusion 3357 located at an end of the cantilever arm 3355. Depending on the corresponding engagement means, the protrusions 3357 may be outwardly facing (as shown in FIGS. 5A and 5B) or inwardly facing. As the hook tab 3322 is pulled, this causes tension to be applied to the resilient carrier 3362, 3364, which in turn causes the cantilever arms 3355 to move in the direction of pulling. As described in more detail below, this tension may result in relative movement between the extension portion 3364 and the connector portion 3362 of the resilient carrier 3362, 3364. This results in the protrusions 3357 of the cantilever arms 3355 to engage with one or more protrusions or projections 3372 of the first rigid member 3350 such that the protrusions 3357 ride over the protrusions or projections 3372 and the cantilever arm 3355 is deflected. Eventually, once the cantilever arms 3355 travel a threshold distance, the cantilever arms 3355 snap back and strike the surface of the first rigid member 3350 to cause an audible alert to the user that a tension limit has been reached, to thus prevent over-tightening of the strap 3320.

The protrusions 3357 are sized such that when they snap back and strike the surface of the first rigid member 3350, an audible sound is produced. For example, as the protrusion 3357 rides over the projection 3372, the cantilever 3355 and protrusion 3357 are pushed into a deflected position. The protrusion 3357 moves resiliently and/or elastically into the deflected position. As the protrusion rides past the projection 3372, it is released from the deflected position into a relaxed position, the movement of which causes the cantilever 3355 to strike the surface of the projection 3372 to produce the audible sound. The intensity of the audible sound may, for example, be dependent on the distance travelled by the cantilever and/or protrusion between the deflected position and the relaxed position. This in turn may be dependent on the height 3374 of the protrusion 3357 relative to the cantilever 3355. In some forms, the height 3374 may be about 0.1 mm to about 10 cm. In some forms, the height 3374 may be about 0.5 mm to about 5 cm. In some forms, the height 3374 may be about 1 mm to about 1 cm. A greater height allows for a substantial snapping back of the cantilever arm 3355 such that the striking of the cantilever arm 3355 onto the projection 3372 is substantial enough to produce an audible sound. The inner end 3376 of the protrusion 3357 may also have a sloping face 3377, with a gradient of about 1° to about 60°. In some forms, the gradient may be about 10° to about 45°. In some forms, the gradient may be about 15° to about 30°, preferably about 30°. This facilitates the release of the second rigid member 3355 from the first rigid member 3350.

The rigidity of the second rigid member 3355, 3356 is constructed and arranged such that the striking of the surface of the first rigid member 3350 may cause an audible alert. Striking the surface of the first rigid member 3350 may also cause a tactile alert, particularly if the patient is wearing the headgear 3300 when the striking occurs. For example, the vibrations that contribute to the audible alert may also be felt by the patient, which could provide a benefit for hearing-impaired patients. In particular, the degree to which the second rigid member 3355, 3356 may resiliently flex may be provided by a Young's modulus value. This may be obtained from a slope of a linear elastic region of a stress-strain curve, where Hooke's law is generally obeyed. Another way may be to characterise the second rigid member 3355, 3356 by its yield strength, the point where a material begins to deform plastically. Any material which allows the second rigid member 3355, 3356 to resiliently flex may be used.

The resilient carrier 3362, 3364 is constructed and arranged such that the threshold distance corresponds to a desired tension limit for the strap. In particular, the degree to which the resilient carrier 3362, 3364 may be stretched, and thus the maximum distance that the second rigid member 3355, 3356 may travel, may be controlled by the dimensions (e.g. the thickness) and/or the Shore hardness (equivalently, flexural modulus) of the resilient carrier 3362, 3364.

The tension limit may be controlled via several factors. These factors, such as surface area, force applied, the corresponding Young's modulus (may be derived from Shore Hardness) of the choice of material and the initial length of the resilient carrier 3362 may influence the stretch of the resilient carrier 3362, 3364 when tension is applied to the headgear (such as, when the hook tab 3322 is pulled). The resilient carrier 3362 may be deformed by a measurement given by a total elastic deformation. The total elastic deformation of the resilient carrier 3362 ($dl_{total}$) is the sum of the horizontal elastic deformation 3380 ($dl_{horizontal}$) and the perpendicular elastic deformation 3378A, 3378B ($dl_{perpendicular}$), as represented by the formula below:

$$dl_{total} = dl_{horizontal} + dl_{perpendicular}$$

The first rigid member 3350 may comprise a channel 3370 within which the second rigid member 3355, 3356 is slidingly movable. The channel 3370 may have sidewalls from which extend projections 3372 that are arranged to engage with the protrusions 3357 of the cantilever arms 3355 to cause the cantilever arms 3355 to deflect inwardly (towards the centre of the channel 3370), as shown in the middle panel of FIG. 5B.

As shown in FIGS. 5A and 5B, the projections 3372 of the first rigid member 3350 are located at the end of the first rigid member 3350, such that once the threshold distance is reached, the protrusions 3357 of the cantilever arms 3355 protrude beyond the end of the first rigid member 3350. This provides a visual indication that the tension limit has been exceeded, in addition to the audible alert caused by the snapping motion of the C-clip 3355 as the protrusions 3357 travel over the projections 3372. It will be appreciated, though, that other configurations are possible. For example, projections 3372 may be located at intermediate locations of the sidewalls of the channel 3370. Additionally, the visual indication could also include an alternate color being exposed as a result of the cantilever arms protruding beyond the end of the first rigid member 3350.

In another variant, which is not shown, projections 3372 need not be located on the sidewalls of the channel 3370, but may be located within the channel 3370 itself. In this variant, the protrusions 3357 of the cantilever arms 3355 do not face towards the sidewalls, but instead face towards a centre of the channel 3370, such that they deflect outwardly (i.e., away from the centre and towards the sidewalls) when hook tab 3322 is pulled.

The resilient carrier 3362, 3364 may comprise a connector portion 3362 that is used to couple the resilient carrier to the first rigid member 3350. For example, the connector portion 3362 may comprise an embedded rigid connector 3360 (which is separate from second rigid member 3355, 3356) and may have an aperture that is shaped such that the connector portion 3362 may be fitted over a boss 3351 located in the channel 3370 of the first rigid member 3350. The boss 3351 may have a substantially rectangular surface. In some forms, the width of the boss 3351 may be variable. For example, some examples of the boss 3351 may include a wider portion distal to the opening of the channel 3370 (i.e., proximate to the projections 3372). The resilient carrier may also comprise an extension portion 3364, for example in the form of a tongue as shown in FIG. 5A, that carries the C-clip 3355, 3356. The extension portion 3364 may be movable relative to the connector portion 3362. For example, engagement between the boss 3351 and the connector portion 3362 may fix the connector portion and a tensile force applied to the hook tab 3322 may move the extension portion 3364 relative to the connector portion 3362.

In some forms, the boss 3351 may extend from the surface of the channel 3370. The boss 3351 may not extend beyond the top of the channel 3370 so that the height of the boss 3351 (e.g., the distance from the surface of the channel 3370 to the top of the boss 3351) is not wider than the first rigid member 3350, although in other examples the height of the boss 3351 may extend beyond the width of the first rigid member 3350.

The provision of the resilient carrier allows for at least a partial decoupling of a pulling force exerted by the user. When the hook material 3322 is pulled, the pulling force is transmitted to the second rigid member 3355, 3356 such that the protrusion 3357 on the second rigid member engages the projection 3372 on the first rigid member when a minimum amount of force is exerted (for example when the retention force reaches about 16 N). Further pulling force exerted on the hook material 3322 is transmitted and dissipated by the resilient carrier due to its elasticity and/or toughness (e.g., when the pulling force exceeds about 16 N). This prevents the user from overtightening the strap while also provides a larger range of the pulling force.

The end portions 3331 of the lower straps 3330 may be constructed substantially identically to the end portions 3321 of upper straps 3320. In some forms of the present technology, it may be desirable to have a different tension limit for the upper straps 3320 than the lower straps 3330. If so, the resilient carrier 3362, 3364 of the upper and lower straps 3320, 3330 may be constructed in a manner that provides different tension limits.

The hook material 3322 and first rigid member 3350 may be made of any suitable polymer. The elasticity and/or rigidity of the polymer should be sufficient for the second rigid member 3355, 3356 to ride over the first rigid member 3350 when the hook material 3322 is pulled. The second rigid member 3355, 3356 may be made of any suitable polymer such as polyethylene, polypropylene, polyurethane or polyethylene terephthalate (PET). Advantageously, the suitable polymer is resiliently flexible and sufficiently tough. The resilient carrier 3362, 3364 may be made from a silicone based material or elastomer. Examples of elastomers include, but is not limited to, polyisoprene, polybutadiene, chloroprene rubber, polychloroprene, Neoprene, Baypren, butyl rubber, styrene-butadiene rubber, nitrile rubber, ethylene propylene rubber, epichlorohydrin rubber, polyacrylic rubber, silicone rubber, fluorosilicone rubber, fluoroelastomers, polyether block amides, chlorosulfonated polyethylene, and ethylene-vinyl acetate.

Turning now to FIG. 6A to 6D, an exemplary method of manufacturing a headgear strap 3320 will be described.

In a first step, as illustrated schematically in FIG. 6A, a strip of material may be cut into a desired shape by any suitable means, such as by an ultrasonic or radio frequency cutting device. The illustrated shape may comprise a linear portion 3320a and a tongue 3320b extending from and having a smaller width than the linear portion 3320a, although any other shape may be used.

Next, as shown in FIG. 6B, an insert molding process may be used to attach the first rigid member 3350 to the strip of material, such that the first rigid member 3350 is over-moulded on the tongue 3320b. As shown in FIG. 6D, the tongue 3320b may be completely covered as a result of the molding process.

Separately, as shown in FIG. 6C, the second rigid member 3355, 3356, resilient carrier 3362, 3364, and hook tab 3322 may be assembled together. The base 3362 is insert-moulded over the rigid connector 3360, and the tongue 3364 is insert-moulded at one end over the C-clip 3355, 3356 and at the other end over an end of the hook tab 3322. The base 3362 may similarly be insert-moulded to the second rigid member 3355, 3356 (although other means of connection, like an interlock method, may be used). When insert moulding the base 3362, an aperture 3353 is formed that extends through the rigid connector 3360.

Finally, as shown in FIG. 6D, the strap 3320 may be assembled by fitting the base 3362/rigid connector 3360 over the boss 3351 of channel 3370 in the first rigid member 3350. For example, the aperture 3353 may be aligned with the boss 3351 so that the boss 3351 may be received through the aperture 3353.

As described above, certain forms of the boss 3351 may have a variable width, specifically with a wider portion distal to the channel. The aperture 3353 may be slightly smaller than the widest portion of the boss 3351. As part of assembling the rigid connector 3360 to the first rigid member 3350, the rigid connector 3360 may snap to the first rigid member 3350 as a result of the smaller aperture 3353 passing around the larger boss 3351. This may result in a snap-fit connector that secures the first rigid member 3350 and the rigid connector 3360 together. In some forms, the rigid connector 3360 and the first rigid member 3350 may be removable from one another.

Figure 7A:
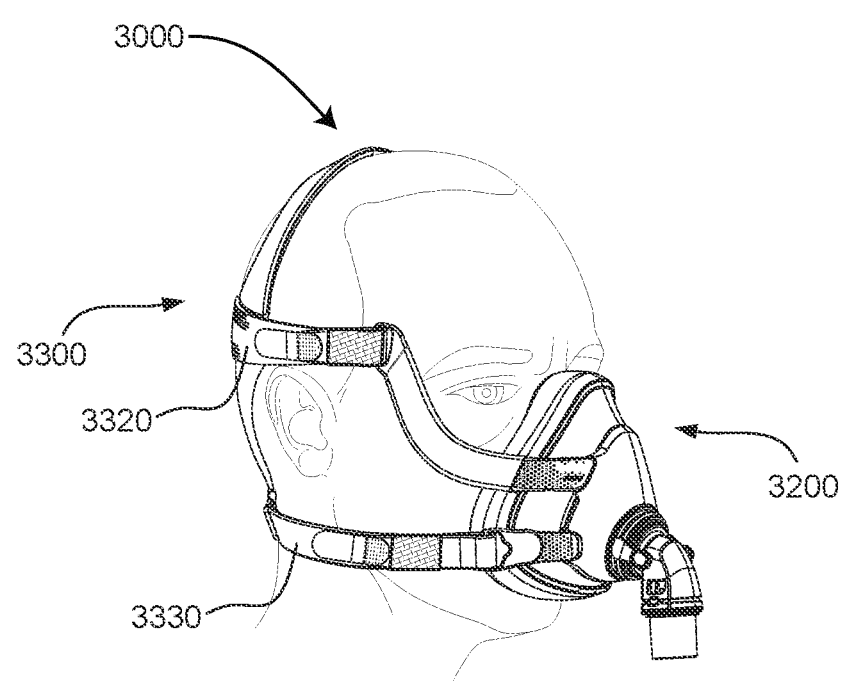
Figure 7B:
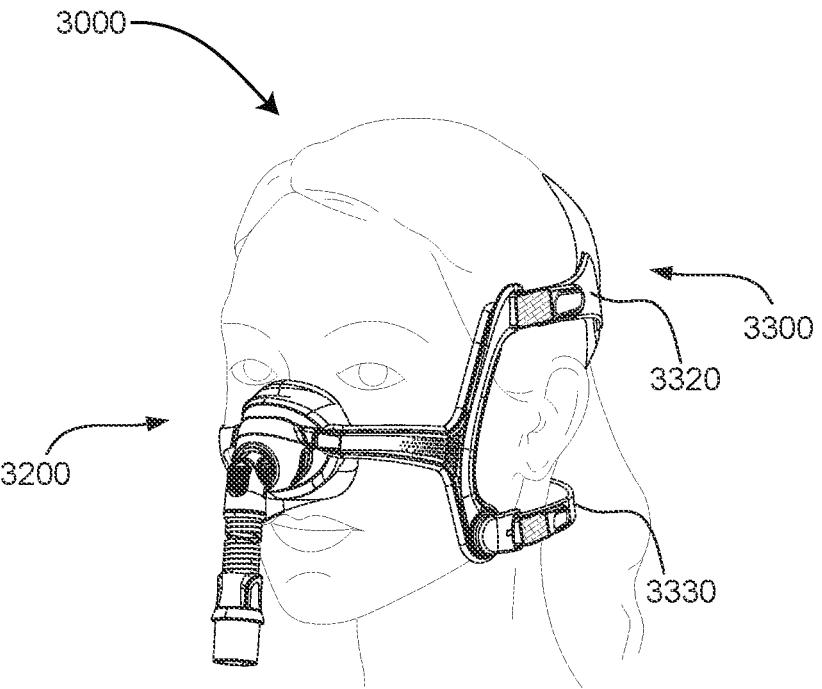
Figure 7C:
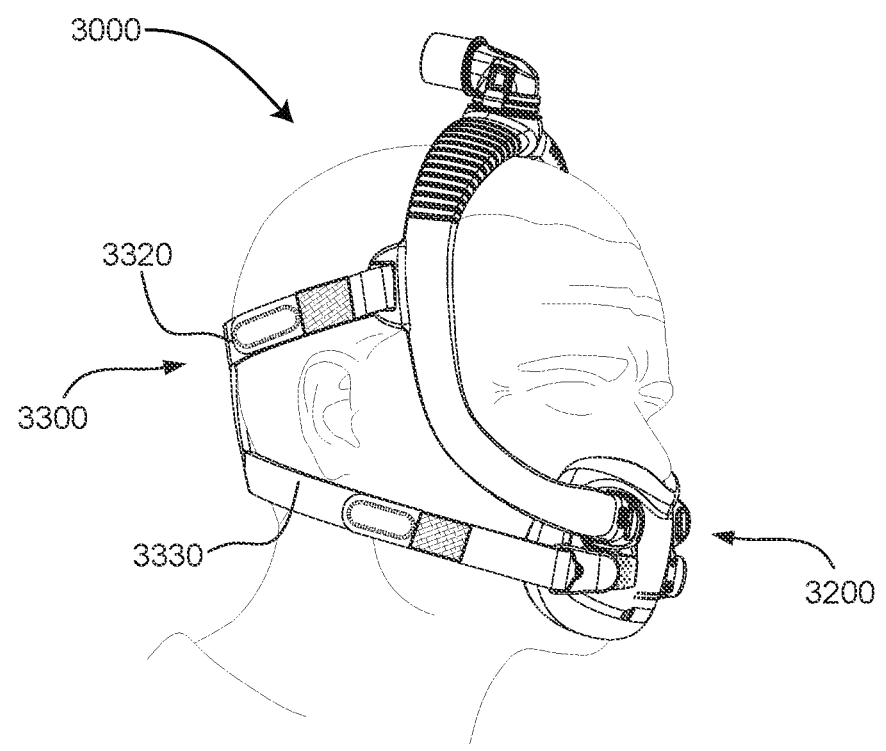
Figure 7D:
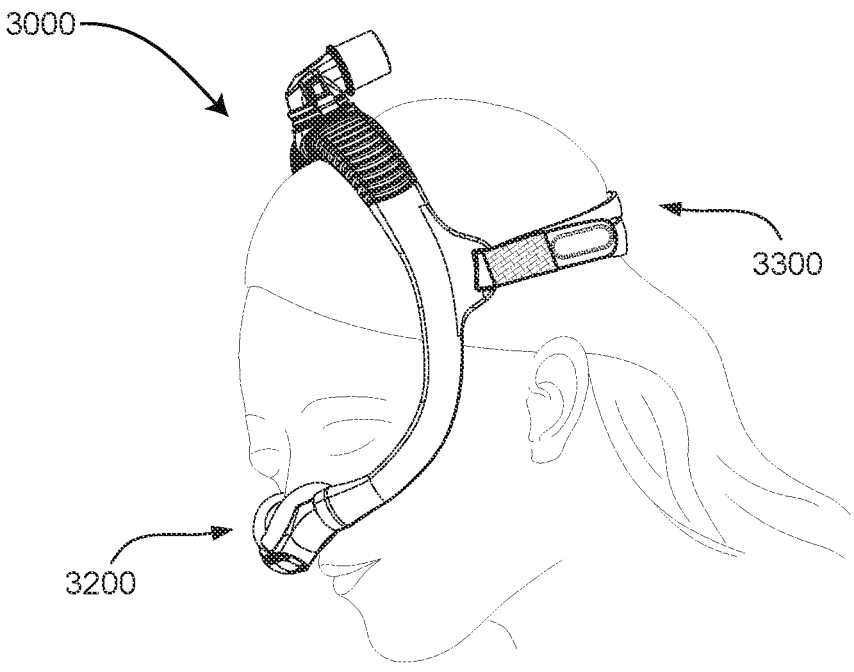

Straps 3320 or 3330 having a tension limit detection feature have been described above with reference to the headgear 3300 shown in FIG. 3A and FIG. 4. However, it will be appreciated that the same principles may be applied to straps of a wide variety of other headgear, such as headgear with both upper and lower straps of various kinds as shown in FIGS. 7A, 7B and 7C, or headgear with only a single strap as shown in FIG. 7D. It will be appreciated that the strap tension suitable for retention of the mask in a therapeutically effective position will vary in these different patient interfaces, and that the properties of the resilient carrier of the strap may be varied accordingly to provide the appropriate tension limit detection.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms for application of respiratory therapy. The RPT device 4000 may be configured to generate a flow of air for delivery to a patient's airways, such as to treat one or more of the respiratory conditions described elsewhere in the present document.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

6 ASPECTS OF THE DISCLOSURE

A1. Headgear for a patient interface, the headgear comprising: one or more straps each having a first end for connecting to a mask; wherein the first end of at least one of the one or more straps comprises: a connection portion, the connection portion being grippable by a user to pull the strap to increase a tension in the strap; a first rigid member; and a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance; wherein the resilient carrier is constructed and arranged such that the threshold distance corresponds to a desired tension limit for the strap.

A2. Headgear according to aspect A1, wherein the first rigid member comprises a channel within which the second rigid member is slidingly movable.

A3. Headgear according to aspect A2, wherein the at least part of the second rigid member comprises a projection located at an end of a cantilever arm.

A4. Headgear according to aspect A3, wherein the second rigid member is a C-clip.

A5. Headgear according to any one of aspects A1 to A4, wherein the desired tension limit is about 16 N, and wherein the resilient carrier comprises an elastomer configured to facilitate elastic deformation relative to the first rigid member.

A6. Headgear according to any one of aspects A1 to A5, wherein the resilient carrier is dimensioned to provide the desired tension limit, and/or is formed from a material having a Shore hardness that provides the desired tension limit.

A7. Headgear according to any one of aspects A1 to A6, wherein the second rigid member is at least partly embedded in the resilient carrier.

A8. Headgear according to any one of aspects A1 to A7, wherein the resilient carrier is connected to the first rigid member via a rigid interface that is separate from the second rigid member.

A9. Headgear according to aspect A8, wherein the rigid interface is embedded in the resilient carrier.

A10. Headgear according to any one of aspects A1 to A9, wherein the one or more straps comprise at least one top strap and at least one bottom strap, and wherein a tension limit for the at least one top strap is different than a tension limit for the at least one bottom strap.

A11. Headgear according to any one of aspects A1 to A10, wherein the connection portion is a hook tab.

A12. Headgear according to any one of aspects A1 to A11, wherein the first rigid member includes a channel with a boss extending from a surface of the channel, and wherein the second rigid member includes an aperture, the second rigid member being receivable within the channel and the boss being receivable within the aperture.

A13. Headgear according to aspect A12, wherein the boss is removably receivable within the aperture.

A14. Headgear according to any one of aspects A1 to A13, wherein the second rigid member is movable between a deflected position and a relaxed position, and wherein when the second rigid member travels further than the threshold distance, the second rigid member moves from the deflected position to the relaxed position.

A15. Headgear according to any one of aspects A1 to A14, wherein the second rigid member includes at least one protrusion and the first rigid member includes at least one projection, wherein contact between the at least one protrusion and the at least one projection is configured to cause the second rigid member to deflect.

B1. Headgear for a patient interface, the headgear comprising: one or more straps each having a first end for connecting to a mask; wherein the first end of at least one of the one or more straps comprises: a connection portion, the connection portion being grippable by a user to pull the strap to increase a tension in the strap; a first rigid member; and a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance; wherein the resilient carrier is constructed and arranged such that the threshold distance corresponds to a desired tension limit for the strap.

B2. Headgear according to aspect B1, wherein the first rigid member comprises a channel within which the second rigid member is slidingly movable.

B3. Headgear according to aspect B2, wherein the at least part of the second rigid member comprises a projection located at an end of a cantilever arm.

B4. Headgear according to aspect B3, wherein the second rigid member is a C-clip.

B5. Headgear according to aspect B1, wherein the desired tension limit is about 16 N, and wherein the resilient carrier comprises an elastomer configured to facilitate elastic deformation relative to the first rigid member.

B6. Headgear according to aspect B1, wherein the resilient carrier is dimensioned to provide the desired tension limit, and/or is formed from a material having a Shore hardness that provides the desired tension limit.

B7. Headgear according to aspect B1, wherein the second rigid member is at least partly embedded in the resilient carrier.

B8. Headgear according to aspect B1, wherein the resilient carrier is connected to the first rigid member via a rigid interface that is separate from the second rigid member.

B9. Headgear according to aspect B8, wherein the rigid interface is embedded in the resilient carrier.

B10. Headgear according to aspect B1, wherein the one or more straps comprise at least one top strap and at least one bottom strap, and wherein a tension limit for the at least one top strap is different than a tension limit for the at least one bottom strap.

B11. Headgear according to aspect B1, wherein the connection portion is a hook tab.

B12. Headgear according to aspect B1, wherein the first rigid member includes a channel with a boss extending from a surface of the channel, and wherein the second rigid member includes an aperture, the second rigid member being receivable within the channel and the boss being receivable within the aperture.

B13. Headgear according to aspect B12, wherein the boss is removably receivable within the aperture.

B14. Headgear according to aspect B1, wherein the second rigid member is movable between a deflected position and a relaxed position, and wherein when the second rigid member travels further than the threshold distance, the second rigid member moves from the deflected position to the relaxed position.

B15. Headgear according to aspect B1, wherein the second rigid member includes at least one protrusion and the first rigid member includes at least one projection, wherein contact between the at least one protrusion and the at least one projection is configured to cause the second rigid member to deflect.

B16. Headgear according to aspect B15, wherein the protrusion has a height of about 1 mm to about 1 cm.

B17. Headgear according to aspect B1, wherein: the second rigid member is a C-clip and is at least partly embedded in the resilient carrier; and the resilient carrier is connected to the first rigid member via a rigid interface that is separate from the second rigid member.

B18. Headgear according to aspect B1, wherein: the one or more straps comprise at least one top strap and at least one bottom strap, and wherein a tension limit for the at least one top strap is different than a tension limit for the at least one bottom strap; the resilient carrier comprises an elastomer configured to facilitate elastic deformation relative to the first rigid member; and the connection portion is a hook tab.

B19. Headgear according to aspect B1, wherein: the first rigid member includes a channel with a boss extending from a surface of the channel, and the first rigid member includes at least one projection; the second rigid member is a C-clip and includes a pair of cantilever arms, the at least part of the second rigid member comprises a projection located at least one of the pair of cantilever arms; the second rigid member further includes an aperture, the second rigid member being receivable within the channel and the boss being receivable within the aperture; and the second rigid member further includes at least one protrusion, wherein contact between the at least one protrusion and the at least one projection is configured to cause the second rigid member to deflect.

B20. The headgear of aspect B1, wherein the first rigid member comprises a channel within which the second rigid member is slidingly movable; the resilient carrier is connected to the first rigid member via a rigid interface that is separate from the second rigid member; the second rigid member is movable between a deflected position and a relaxed position, and wherein when the second rigid member travels further than the threshold distance, the second rigid member moves from the deflected position to the relaxed position; and the second rigid member includes at least one protrusion and the first rigid member includes at least one projection, wherein contact between the at least one protrusion and the at least one projection is configured to cause the second rigid member to deflect.

C1. Headgear for a patient interface, the headgear comprising: one or more straps each having a first end for connecting to a mask; wherein the first end of each strap comprises: a second rigid member that is connected to the connection portion, the second rigid member being movable relative to the first rigid member when the connection portion is pulled by the user, wherein at least part of the second rigid member is arranged to output an alert when the second rigid member travels further than a threshold distance, and wherein the second rigid member is movable between a deflected position and a relaxed position, and wherein when the second rigid member travels further than the threshold distance, the second rigid member moves from the deflected position to the relaxed position.

C2. Headgear for the patient interface of aspect C1, wherein the second rigid member extends from a resilient carrier that is connected to the connection portion; and wherein the resilient carrier is constructed and arranged such that the threshold distance corresponds to a desired tension limit for the strap.

C3. Headgear according to aspect C2, wherein the second rigid member is at least partly embedded in the resilient carrier.

C4. Headgear according to any one of aspects C2 to C3, wherein the resilient carrier is connected to the first rigid member via a rigid interface that is separate from the second rigid member.

C5. Headgear according to aspect C4, wherein the rigid interface is embedded in the resilient carrier C6. Headgear according to any one of aspects C1 to C5, wherein the first rigid member comprises a channel within which the second rigid member is slidingly movable.

C7. Headgear according to any one of aspects C1 to C6, wherein the at least part of the second rigid member comprises a projection located at an end of a cantilever arm.

C8. Headgear according to any one of aspects C1 to C7, wherein the second rigid member is a C-clip.

C9. Headgear according to any one of aspects C1 to C8, wherein the one or more straps comprise at least one top strap and at least one bottom strap, and wherein a desired tension limit for the at least one top strap is different than a desired tension limit for the at least one bottom strap.

C10. Headgear according to any one of aspects C1 to C9, wherein the connection portion is a hook tab.

C11. Headgear according to any one of aspects C1 to C10, wherein the first rigid member includes a channel with a boss extending from a surface of the channel, and wherein the second rigid member includes an aperture, the second rigid member being receivable within the channel and the boss being receivable within the aperture.

C12. Headgear according to aspect C11, wherein the boss is removably receivable within the aperture.

C13. Headgear according to any one of aspects C1 to C12, wherein the second rigid member is movable between a deflected position and a relaxed position, and wherein when the second rigid member travels further than the threshold distance, the second rigid member moves from the deflected position to the relaxed position.

C14. Headgear according to any one of aspects C1 to C13, wherein the second rigid member includes at least one protrusion and the first rigid member includes at least one projection, wherein contact between the at least one protrusion and the at least one projection is configured to cause the second rigid member to deflect.

7 GLOSSARY

For the purposes of the present technology disclosure, in certain forms of the present technology, one or more of the following definitions may apply. In other forms of the present technology, alternative definitions may apply.

7.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

Textile: A flexible material formed from a network of fibres, which may be natural, artificial, or a combination thereof. The fibres (e.g. wool, flax, cotton, hemp, and/or artificial fibres) may be spun into a yarn that is woven, knitted, crocheted, knotted, tatted, felted, and/or braided to form the textile. As used herein, the terms "textile" and "fabric" are interchangeable.

7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

7.2 Patient Interface

Anti-asphyxia valve (AAV): The component or sub-assembly of a mask system that, by opening to atmosphere in a failsafe manner, reduces the risk of excessive CO2 rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

7.3 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. Headgear for a patient interface, the headgear comprising:
   one or more straps each having a first end for connecting to a mask;
   wherein the first end of at least one of the one or more straps comprises:
   a connection portion, the connection portion being grippable by a user to pull the strap to increase a tension in the strap;
   a first rigid member; and
   a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance;
   wherein the resilient carrier is constructed and arranged such that the threshold distance corresponds to a desired tension limit for the strap, and
   wherein the second rigid member is at least partly embedded in the resilient carrier.

2. Headgear according to claim 1, wherein the first rigid member comprises a channel within which the second rigid member is slidingly movable.

3. Headgear according to claim 2, wherein the at least part of the second rigid member comprises a projection located at an end of a cantilever arm.

4. Headgear according to claim 3, wherein the second rigid member is a C-clip.

5. Headgear according to claim 1, wherein the resilient carrier comprises an elastomer configured to facilitate elastic deformation relative to the first rigid member.

6. Headgear according to claim 1, wherein the desired tension limit is about 16 N, and wherein the resilient carrier is dimensioned to provide the desired tension limit, and/or is formed from a material having a Shore hardness that provides the desired tension limit.

7. Headgear according to claim 1, wherein the connection portion is a hook tab.

8. Headgear according to claim 1, wherein the first rigid member includes a channel with a boss extending from a surface of the channel, and wherein the second rigid member includes an aperture, the second rigid member being receivable within the channel and the boss being receivable within the aperture.

9. Headgear according to claim 8, wherein the boss is removably receivable within the aperture.

10. Headgear according to claim 1, wherein the second rigid member is movable between a deflected position and a relaxed position, and wherein when the second rigid member travels further than the threshold distance, the second rigid member moves from the deflected position to the relaxed position.

11. Headgear according to claim 1, wherein the second rigid member includes at least one protrusion and the first rigid member includes at least one projection, wherein contact between the at least one protrusion and the at least one projection is configured to cause the second rigid member to deflect.

12. Headgear according to claim 11, wherein the protrusion has a height of about 1 mm to about 1 cm.

13. Headgear according to claim 1, wherein:

the one or more straps comprise at least one top strap and at least one bottom strap, and wherein a tension limit for the at least one top strap is different than a tension limit for the at least one bottom strap;

the resilient carrier comprises an elastomer configured to facilitate elastic deformation relative to the first rigid member; and the connection portion is a hook tab.

14. Headgear according to claim 1, wherein:

the first rigid member includes a channel with a boss extending from a surface of the channel, and the first rigid member includes at least one projection;

the second rigid member is a C-clip and includes a pair of cantilever arms, the at least part of the second rigid member comprises a projection located on at least one of the pair of cantilever arms;

the second rigid member further includes an aperture, the second rigid member being receivable within the channel and the boss being receivable within the aperture; and the second rigid member further includes at least one protrusion, wherein contact between the at least one protrusion and the at least one projection of the first rigid member is configured to cause the second rigid member to deflect.

15. Headgear for a patient interface, the headgear comprising:

one or more straps each having a first end for connecting to a mask;

wherein the first end of at least one of the one or more straps comprises:

a connection portion, the connection portion being grippable by a user to pull the strap to increase a tension in the strap;

a first rigid member; and a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance;

wherein the resilient carrier is constructed and arranged such that the threshold distance corresponds to a desired tension limit for the strap, and wherein the resilient carrier is connected to the first rigid member via a rigid interface that is separate from the second rigid member.

16. Headgear according to claim 15, wherein the rigid interface is embedded in the resilient carrier.

17. Headgear according to claim 16, wherein the one or more straps comprise at least one top strap and at least one bottom strap, and wherein a tension limit for the at least one top strap is different than a tension limit for the at least one bottom strap.

18. Headgear for a patient interface, the headgear comprising:

one or more straps each having a first end for connecting to a mask;

wherein the first end of at least one of the one or more straps comprises:

a connection portion, the connection portion being grippable by a user to pull the strap to increase a tension in the strap;

a first rigid member; and a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance;

wherein the resilient carrier is constructed and arranged such that the threshold distance corresponds to a desired tension limit for the strap, and wherein:

the second rigid member is a C-clip and is at least partly embedded in the resilient carrier; and the resilient carrier is connected to the first rigid member via a rigid interface that is separate from the second rigid member.

19. Headgear for a patient interface, the headgear comprising:

one or more straps each having a first end for connecting to a mask;

wherein the first end of at least one of the one or more straps comprises:

a connection portion, the connection portion being grippable by a user to pull the strap to increase a tension in the strap;

a first rigid member; and a second rigid member that extends from a resilient carrier that is connected to the connection portion, the second rigid member being movable relative to the first rigid member when the connection portion is pulled by the user, wherein at least part of the second rigid member is arranged to strike the first rigid member to cause at least an audible alert when the second rigid member travels further than a threshold distance;

wherein the resilient carrier is constructed and arranged such that the threshold distance corresponds to a desired tension limit for the strap and, wherein the first rigid member comprises a channel within which the second rigid member is slidingly movable;

the resilient carrier is connected to the first rigid member via a rigid interface that is separate from the second rigid member;

the second rigid member is movable between a deflected position and a relaxed position, and wherein when the second rigid member travels further than the threshold distance, the second rigid member moves from the deflected position to the relaxed position; and the second rigid member includes at least one protrusion and the first rigid member includes at least one projection, wherein contact between the at least one protrusion and the at least one projection is configured to cause the second rigid member to deflect.

\* \* \* \* \*